US009944936B2

(12) United States Patent
Ezura et al.

(10) Patent No.: US 9,944,936 B2
(45) Date of Patent: Apr. 17, 2018

(54) *AGROBACTERIUM* HAVING HIGHLY EFFICIENT GENE TRANSFER ABILITY TO PLANT IMPARTED THERETO

(71) Applicant: UNIVERSITY OF TSUKUBA, Tsukuba-shi, Ibaraki (JP)

(72) Inventors: Hiroshi Ezura, Tsukuba (JP); Koji Nakamura, Tsukuba (JP); Satoko Nonaka, Tsukuba (JP); Tatsuhiko Someya, Tsukuba (JP); Sha Zhou, Tsukuba (JP)

(73) Assignee: UNIVERSITY OF TSUKUBA, Tsukuba-Shi, Ibaraki (JP)

( * ) Notice: Subject to any disclaimer, the term of this patent is extended or adjusted under 35 U.S.C. 154(b) by 314 days.

(21) Appl. No.: 14/766,340

(22) PCT Filed: Feb. 7, 2014

(86) PCT No.: PCT/JP2014/052844
§ 371 (c)(1),
(2) Date: Aug. 6, 2015

(87) PCT Pub. No.: WO2014/123208
PCT Pub. Date: Aug. 14, 2014

(65) Prior Publication Data
US 2015/0368658 A1 Dec. 24, 2015

(30) Foreign Application Priority Data
Feb. 8, 2013 (JP) .................................. 2013-023726

(51) Int. Cl.
*C12N 15/82* (2006.01)
*C12N 9/10* (2006.01)
*C12N 9/78* (2006.01)

(52) U.S. Cl.
CPC ....... *C12N 15/8205* (2013.01); *C12N 9/1096* (2013.01); *C12N 9/78* (2013.01); *C12Y 206/01019* (2013.01); *C12Y 305/99007* (2013.01)

(58) Field of Classification Search
None
See application file for complete search history.

(56) References Cited

FOREIGN PATENT DOCUMENTS

JP 2005-312345 A 11/2005
JP 2013-183659 A 9/2013

OTHER PUBLICATIONS

Hao et al (ACC deaminase increases the Agrobacterium tumefaciens-mediated Transformation frequency of commercial canola cultivars. FEMS Microbiol Lett. 307, 185-190, 2010).*
Chevrot et al (GABA controls the level of quorum-sensing signal in Agrobacterium tumefaciens. Proc. Natl. Acad. Sci. USA 103, 7460-7464, 2006).*
Haudecoeur et al (Proline antagonizes GABA-induced quenching of quorum-sensing in Agrobacterium tumefaciens. Proc. Natl. Acad. Sci. USA 106, 14587-14592, 2009).*
Yuan et al (Comparative transcriptome analysis of Agrobacterium tumefaciens in response to plant signal salicylic acid, indole-3-acetic acid and g-amino butyric acid reveals signaling cross-talk and Agrobacterium—plant co-evolution. Cellular Microbiology. 10, 2339-2354, 2008).*
Bartsch et al (Molecular Analysis of Two Genes of the *Escherichia coli* gab Cluster: Nucleotide Sequence of the Glutamate:Succinic Semialdehyde Transaminase Gene (gabT) and Characterization of the Succinic Semialdehyde Dehydrogenase Gene (gabD). Journal of Bacteriology. p. 7035-7042, Dec. 1990).*
Chevrot, R. et al., "GABA Controls the Level of Quorum-Sensing Signal in *Agrobacterium Tumefaciens*", *PNAS*, vol. 103, No. 19, May 9, 2006, pp. 7460-7464.
Haudercoeur, E. et al., "Proline Antagonizes GABA-Induced Quenching of Quorum-Sensing in *Agrobacterium Tumefaciens*", *PNAS*, vol. 106, No. 34, Aug. 25, 2009, pp. 14587-14592.
Nonaka, S. et al., "1-Aminocyclopropane-1-Carboxylate Deaminase Enhances *Agrobacterium Tumefaciens*-Mediated Gene Transfer Into Plant Cells", *Applied and Environmental Microbiology*, vol. 74, No. 8, Apr. 2008, pp. 2526-2528.
Pappas, K., "Cell-Cell Signaling and the *Agrobacterium Tumefaciens* Ti Plasmid Copy Number Fluctuations", *Plasmid*, vol. 60, 2008, pp. 89-107.
Simpson, J. et al., "γ-Aminobutyrate Transaminase Limits the Catabolism of γ-Aminobutyrate in Cold-Stressed *Arabidopsis* Plants: Insights From an Overexpression Mutant", Botany, vol. 88, 2010, pp. 522-527.
Someya, T. et al., "Study of Convenience and Efficacy of *Agrobacterium* Having an Ethylene Production-Suppressing Enzyme", *Abstracts of the 29th Annual Meeting of the Japanese Society for Plant Cell and Molecular Biology*, 2011, pp. 155, 2Cp-09.
Yuan, Z. et al., "The Plant Signal Salicylic Acid Shuts Down Expression of the Vir Regulon and Activates Quormone-Quenching Genes in *Agrobacterium*", *PNAS*, vol. 104, No. 28, Jul. 10, 2007, pp. 11790-11795.
"4-Aminobutyrate Aminotransferase, PLP-Dependent [*Escherichia coli* DH10B]", Database Genbank [online], Accession No. YP_001731569, https://www.ncbi.nlm.nih.gov/protein/170082249?sat=12&satkey=2926708#feature_170082249_CDS_0, Mar. 17, 2008 [retrieved on Apr. 15, 2014], 1 page.
International Search Report, and English language translation thereof, in corresponding International Application No. PCT/JP2014/052844, dated Apr. 28, 2014, 6 pages.

* cited by examiner

*Primary Examiner* — Medina A Ibrahim
*Assistant Examiner* — Wayne Zhong
(74) *Attorney, Agent, or Firm* — Brinks Gilson & Lione

(57) ABSTRACT

The present invention relates to an *Agrobacterium* having improved gene transfer efficiency. The present invention provides a transformed *Agrobacterium* which harbors a foreign GABA transaminase gene and exhibits improved gene transfer efficiency, and a method for producing a transformed plant using the same.

16 Claims, 8 Drawing Sheets

Fig. 3 atgaccatgattacgccaagcgcgcaattaaccctcactaaagggaacaaaagctgggtaccgggccccccctcgaggtcgac
———————————————————————————————————————————————————————————————————————→
                                                              lacZ partial fragment
ggtatcgataagcttaatgaacagcaataaagagttaatgcagcgccgagtcaggcgatccaggcgattcccgtggcgttggcaaattc
   →  gabT
acccgatttcgctgaccgcgcggaaaactgccggtgtggacgttgaaggccgtgagtatcttgattcgcggcgggatt
gcggtgctcaataccggcacctgcatccgaaggtgtggccgcggtggaagcgcagttgaaaaactgtcgcacacctgctt
ccaggtgctggcttacgagccgtatctggagctgtgtgcgagattatgaatcagaaggtgccggcgattcgccaagaaacgc
tgctggttacgaccggttccgaagcggtgcacgcattacacgctggcgctgaaaaacgcggtaaaaatcgcccgcgccaccaaacgtagcggcaccatcgct
tttagcggcgcgtatcacggtcatgttttatcgcgcgtcttgcccgctgcacggcataagcgaggatgacgctatcgccagcatccacc
gatgccgggtcatgtttatcgcgccgtcttatcgcgcgaagatatcgccgaagatatcgccggaagatatcgccgaagcggtttctacgcc
ggatcttcaaaaatgatgcgccggaagatatcgccggaagatatcgccgaagatatcgccgaaggcggtttctacgcc
tcgtcgcagctttatgcagcgtttacgcgctctcgtgtgacgagcacgggatcatgctgatctgccgatgaagtgcagagcgg
cgcgggggcgtaccggcacgctgtttgcgatggagcagatgggcgttgcgccggatcttgccaccctttgcgaatcgatcgcgg
gcggcttcccgctgccggcgtggcctgcgtggcctggatctggctggtgccggaagtaatgatgcctcgctccaggcggtctgggcgcacctatgcg
ggtaacccgattgcctgccgctgcgtgctgccggatgctggcgatagccgaaagtgtttgagcaggaaaatctgctgcaaaagccaacgatct
ggggcagaagttgaaagacggattgctgcgcgatcacaaccggagatcggcgacgtacgcgggctggggcgatga
tcgccattgagctgtttgaagacggtgttgaagacggattgcacacacccggagatcggcgacgtacgcgggctggggcgatga
aaaggcctgattcttctctctgcggcccgtattacaacgtgctgcgcatccttgtaccgctcaccattgaagacgctcagat
ccgtcaggtctggagatcatcagcagtgttttgatgaggcgaagcagtag

Fig. 4 tctgcgcgtaatctgctgcttgagcgcaacgcaattaatgtgagttagctcactcattaggcaccccaggctttacactttatgctt
*Lac promoter*
ccggctcgtatgttgtgtggaattgtgagcggataacaatttcacacaggaaacagctatgaccatgattacgccaagcgcgcaatt
Ribosomal binding sequence    *lacZ partial fragment*
aaccctcactaaagggaacaaaagctgggtaccgggccccccctcgaggtcgacggtatcgataagcttaatgaacagcaataagaa
*gabT*
gttaatgcagccgccgcagtcaggcgattcccgttgggcaaattcaccgcgatttcgctgaccgcgcggaaactgccggt
gtgggacgttgaaggccgtgagtatcttgatttcgcgggcgggattgcggtgctcaataccgggcacctgcatccgaaggtggtggc
cgcggtggaagcgcagttgccggcgattgaaaaactgtcgcacacctgcttccaggtgctggcttacgacgtgtctggagctgtgcgagattat
gaatcagaagaaggtgccggcgatttcgccaagaaaacgtctgctggttacgaccggttccgaagcggtggaaacgcggtaaaatcgc
ccgcgccgccaccaaacgtagcggcaccatcgcttttagcggcgtatcacggcgcacgcattacacctgccgctgaccggcaa
ggtgaatccgtactctgcgccagcatgggcggctgatgccggtcatgtttatcgcgccggaagatatcgccgccatcgtgattgagccggttca
ggatgacgctatcgcccaccggatccttcaaaaatgatgccgcgcgttacgcgcttatgcagcgtctgtgtgacgagcagatggcgcacggatctgattgc
gggcgaaggcggtttcctacgcgtcgtcgccagccttatgcctgccacggcgtttgcgatggagcagatgggcgttgcgccggatcttaccacctttgc
cgatgaagtgcagagcggcgcttccccgctggcggcgtacccgtggcggtgtcacggcgtggctgccgtctgtcaggtctgggcgg
gaaatcgcatccggcggtaaccggaagttgaaagacggattgcctgctgcggcgatcacaacaagccgaactcaccgagatcggcgacgtacgcggctggggcgat
caccttatgccgcagaagttgaaagacggattgcctgctgcggcgatcacaacaagccgaactcaccgagatcggcgacgtacgcggctggggcgat
cgatctgggcagattgagctgtttgaagacgcgccgccgatagccggatcacccgaaaaacaccgaaaacaccgaaaatctgctgcaaaaggcaa
gatcgccattgagctgtttgaagagacgcgccgccgatagccggatcacccgaaaaacaccgaaaacaccgaaaatctgctgcaaaaggcaa
aggcctgattcctctcctcgcggcccgtattacaacgtgctgcgcatccttgtaccgctcaccattgaagagacgctcagatccgtca
gggtctggagatcatcagccagtgttttgatgaggcgaagcagtagtctagaatcg Fig. 7A
Fig. 7B
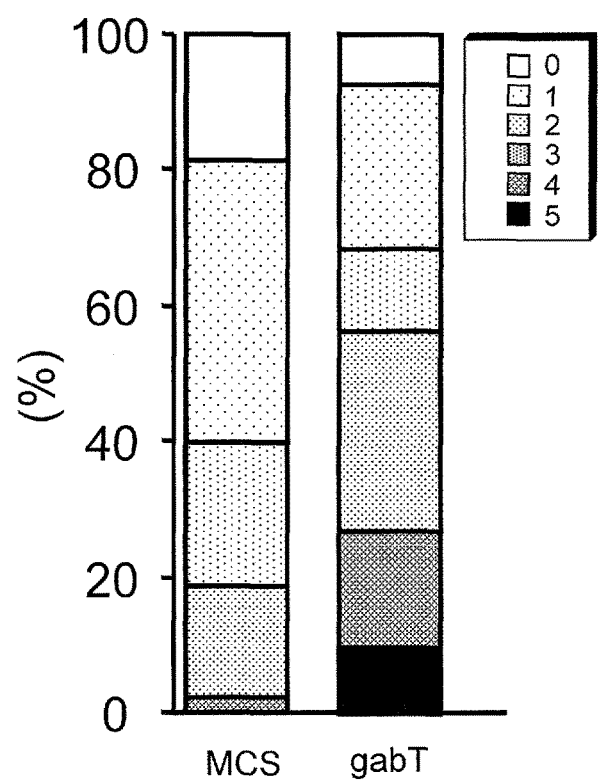
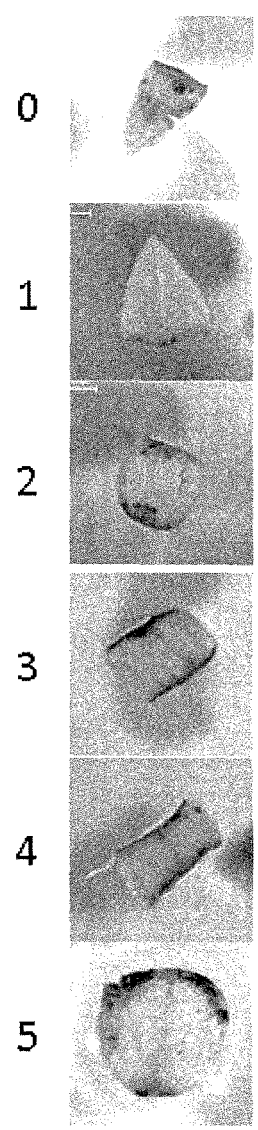

AGROBACTERIUM HAVING HIGHLY EFFICIENT GENE TRANSFER ABILITY TO PLANT IMPARTED THERETO

This application is a 371 application of PCT/JP2014/052844 having an international filing date of Feb. 7, 2014, which claims priority to JP 2013-023726 filed Feb. 8, 2013, the entire contents of which are incorporated herein by reference.

TECHNICAL FIELD

The technique of the present invention relates to *Agrobacterium* having improved gene transfer efficiency to plants, and use thereof.

BACKGROUND ART

A method for gene transfer to plants via *Agrobacterium*, a soil bacterium (*Agrobacterium* method) can be carried out by convenient procedures without the need of special techniques or apparatuses. The *Agrobacterium* method can transfer a gene in a complete form and with a small copy number to a plant. This method is therefore used with high frequency in the preparation of transformed plants, as compared with other plant gene transfer methods. However, on the other hand, there are many plant species having low transfer efficiency by the *Agrobacterium* method. Accordingly, the development of *Agrobacterium* having enhanced gene transfer ability to plants has been demanded.

Super-*Agrobacterium* has been reported, which is *Agrobacterium* having improved gene transfer efficiency to plants by harboring a plasmid containing an ACC deaminase gene imparting the ability to inhibit ethylene production to *Agrobacterium* (Patent Literature 1 and Non Patent Literature 1). The development of *Agrobacterium* having high gene transfer efficiency has still been demanded in order to improve gene transfer efficiency on the basis of various mechanisms. The present inventors have developed a technique of stably improving the gene transfer efficiency of *Agrobacterium* by integrating an ACC deaminase gene into a predetermined region on the genome of *Agrobacterium* (Patent Literature 2).

Meanwhile, GABA (γ-aminobutyric acid) is produced in plants as a result of damages to or *Agrobacterium* infection of the plants (Non Patent Literature 2). Plants highly producing GABA have also been reported to have low susceptibility to infection by an *Agrobacterium tumefaciens* C58 strain (Non Patent Literature 3). Plant GABA is further known to inhibit the quorum sensing signals of *Agrobacterium* and inhibit the replication of Ti plasmids necessary for gene transfer or horizontal transfer among *Agrobacterium* bacteria (Non Patent Literatures 4 and 5). It is, however, unknown whether the GABA activity of plants can be altered by modification of *Agrobacterium* and whether gene transfer efficiency can thereby be changed.

CITATION LIST

Patent Literature

Patent Literature 1: JP Patent Publication (Kokai) No. 2005-312345 A (2005)
Patent Literature 2: JP Patent Publication (Kokai) No. 2013-183659 A (2013)

Non Patent Literature

Non Patent Literature 1: Nonaka et al., Applied and Environmental Microbiology, April (2008) p. 2526-2528
Non Patent Literature 2: Haudecoeur et al., (2009) Proc. Natl. Acad. Sci. USA, 106: 14587-14592
Non Patent Literature 3: Chevrot et al., (2006) Proc. Natl. Acad. Sci. USA, 103: 7460-7464
Non Patent Literature 4: Yuan et al., (2007) Proc. Natl. Acad. Sci. USA, 104: 11790-5
Non Patent Literature 5: Pappas (2008) Plasmid 60: 89-107

SUMMARY OF INVENTION

Technical Problem

An object of the present invention is to provide *Agrobacterium* having high gene transfer efficiency.

Solution to Problem

The present inventors have conducted diligent studies to attain the object and consequently completed the present invention by finding out that the gene transfer efficiency of *Agrobacterium* to plants can be largely improved by imparting GABA transaminase activity to *Agrobacterium*.

Specifically, the present invention encompasses the following:

[1] A transformed *Agrobacterium* which harbors a foreign GABA transaminase gene and exhibits improved gene transfer efficiency.

Also preferably, this transformed *Agrobacterium* of the present invention further harbors a foreign ACC deaminase gene.

Preferably, the transformed *Agrobacterium* of the present invention harbors the GABA transaminase gene and/or the ACC deaminase gene in a vector form.

The transformed *Agrobacterium* of the present invention may further comprise a binary vector comprising a T-DNA region.

In this context, the GABA transaminase gene is preferably derived from a bacterium. Also, the ACC deaminase gene is preferably derived from a bacterium.

[2] A method for producing a transformed plant, comprising carrying out gene transfer to a plant using the transformed *Agrobacterium* according to [1].

In this method, the plant can be a monocotyledon or a dicotyledon. The monocotyledon is preferably, for example, a plant of the family Poaceae. The dicotyledon is preferably, for example, a plant of the family Solanaceae.

The present specification includes the contents described in the specification and drawings of Japanese Patent Application No. 2013-023726 of which the present application claims the priority.

Effects of Invention

The present invention can efficiently transfer a gene of interest to the genome of a plant host.

BRIEF DESCRIPTION OF THE DRAWINGS

FIG. 3 shows a nucleotide sequence encoding a GABA transaminase protein (gabT) in pBBRgabT. In the figure, a region encoding β galactosidase-derived 33 amino acids (lacZ partial fragment) is indicated.

FIG. 4 shows the nucleotide sequence of gabT fragment 2 (SEQ ID NO: 9) amplified by PCR using pBBRgabT as a template and primers acdS-for and gabT-Rev. In the figure, regions of lac promoter, a ribosomal binding sequence (double-underlined), a sequence encoding β galactosidase-derived 33 amino acids (lacZ partial fragment), and a GABA transaminase gene (gabT) (ORF) are indicated.

FIG. 7 shows the gene transfer efficiency of *Agrobacterium* to tomato. FIG. 7A shows the frequency of gene transfer in tomato explants infected by *Agrobacterium*, as the distribution of 6 GUS staining levels. MCS: *Agrobacterium* strain GV2260 (pBBR1MCS-5, pEKH$_2$); and gabT: *Agrobacterium* strain GV2260 (pBBRgabT, pEKH$_2$). FIG. 7B shows examples of GUS staining levels 0 to 5.

DETAILED DESCRIPTION OF THE PREFERRED EMBODIMENTS

Figure 1:
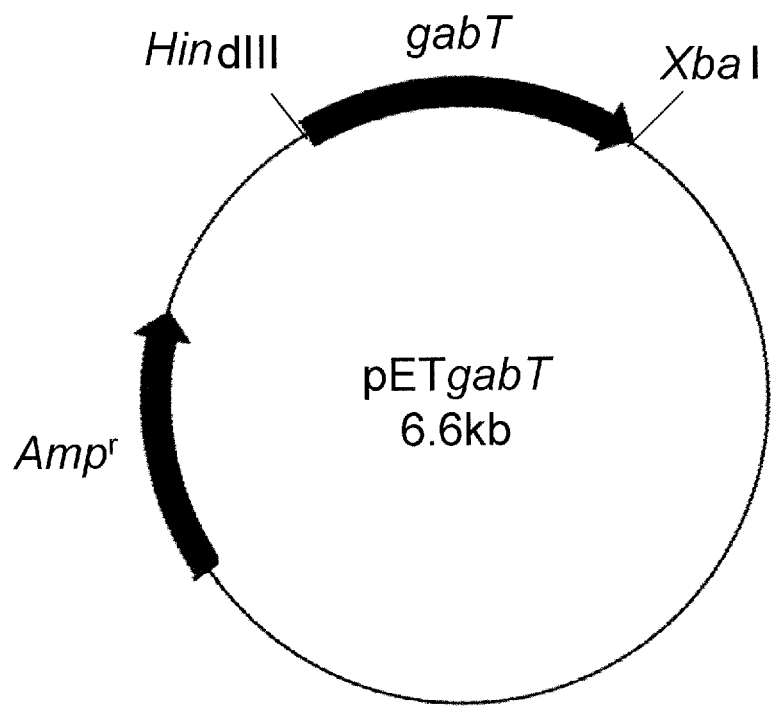
FIG. 1 shows a plasmid map of pETgabT having a GABA transaminase gene (gabT).

Hereinafter, the present invention will be described in detail.

The present invention provides a transformed *Agrobacterium* having improved gene transfer efficiency to plants infected thereby by imparting GABA transaminase activity to *Agrobacterium*. More specifically, the transformed *Agrobacterium* according to the present invention is a transformed *Agrobacterium* harboring a foreign GABA transaminase gene. The transformed *Agrobacterium* according to the present invention exhibits improved gene transfer efficiency to plants in *Agrobacterium*-mediated transformation, as compared with before a gene transfer of the GABA transaminase gene. In the present invention, the "foreign" GABA transaminase gene refers to a GABA transaminase gene exogenously introduced into an *Agrobacterium* bacterium, or a GABA transaminase gene maintained in the progeny of the *Agrobacterium* bacterium.

The GABA transaminase gene used in the present invention is a nucleic acid encoding a GABA transaminase protein. The GABA transaminase has the activity of metabolizing GABA (γ-aminobutyric acid) to succinic semialdehyde and glutamate. A wide range of bacteria including *Escherichia coli*, bacteria of the genus *Pseudomonas*, the genus *Mycobacterium*, root nodule bacteria, and the like as well as plants, etc., are known to have the GABA transaminase gene, whereas naturally occurring *Agrobacterium* lacks a GABA transaminase gene. The GABA transaminase gene used in the present invention may be a gene derived from any organism species (bacteria, plants, fungi, or animals, etc.) having the GABA transaminase. For example, a GABA transaminase gene derived from a bacterium such as a bacterium of the genus *Escherichia* such as *Escherichia coli*, a root nodule bacterium (*Sinorhizobium meliloti*, etc.), a bacterium of the genus *Pseudomonas* (*Pseudomonas syringae*, *Pseudomonas stutzeri*, etc.), a bacterium of the genus *Crinalium* (*Crinalium epipsammum*, etc.), a bacterium of the genus *Cyanobacterium* (*Cyanobacterium aponinum*, etc.), a bacterium of the genus *Streptomyces* (*Streptomyces rimosus*, etc.), a bacterium of the genus *Enterobacter* (*Enterobacter cloacae* subsp., etc.), a bacterium of the genus *Bacillus* (*Bacillus* sp.), a bacterium of the genus *Providencia* (*Providencia stuartii*, etc.), or a bacterium of the genus *Mycobacterium* (*Mycobacterium marinum*, etc.) can be preferably used.

In one embodiment, for example, a nucleic acid fragment comprising a nucleotide sequence encoding the amino acid sequence (SEQ ID NO: 2) of GABA transaminase derived from an *Escherichia coli* K12 strain, for example, a nucleic acid fragment having the nucleotide sequence shown by SEQ ID NO: 1 as an open reading frame (ORF), may be used as the GABA transaminase gene. In the present invention, the open reading frame (ORF) refers to a nucleic acid sequence from a start codon to a stop codon encoding a protein. Alternatively, a nucleic acid fragment consisting of a nucleotide sequence having 70% or more, preferably 80% or more, preferably 85% or more, more preferably 90% or more, for example, 95%, 98%, or 99% or more sequence identity to the nucleotide sequence (full length) shown by SEQ ID NO: 1 and encoding a protein having GABA transaminase activity may be used as the GABA transaminase gene. Also, a nucleic acid fragment consisting of a nucleotide sequence encoding a protein that consists of an amino acid sequence derived from the amino acid sequence shown by SEQ ID NO: 2 by the deletion, substitution, or addition of 1 to 50, preferably 1 to 10, for example, 1 to 5 amino acids and has GABA transaminase activity may be used as the GABA transaminase gene. In addition, a nucleic acid fragment consisting of a nucleotide sequence encoding a protein that consists of an amino acid sequence having 70% or more, preferably 80% or more, preferably 85% or more, more preferably 90% or more, for example, 95%, 98%, or 99% or more sequence identity to the amino acid sequence (full length) shown by SEQ ID NO: 2 and has GABA transaminase activity may be used as the GABA transaminase gene. The GABA transaminase activity can be determined by use of a GABA transaminase activity measurement method known in the art and, for example, can be measured according to a method described in Example 5 mentioned later. Specifically, in the method, the protein is added to a reaction solution (0.1 M Bicine-NaOH, 0.1 M pyridoxal phosphate, 10 mM 2-ketoglutarate, and 10 mM GABA) and incubated at 37° C. to react them. After a given reaction time, the amount of glutamate, which is a reaction product of the GABA transaminase reaction, can be measured. The amount of glutamate may be measured using, but not limited to, any commercially available kit that exhibits sufficient measurement sensitivity, for example, YAMASA L-Glutamate Assay Kit II (Yamasa Corp.). If increase over time in the amount of glutamate is detected, it can be concluded that GABA transaminase activity has been determined. In the present invention, the "nucleic acid fragment" may be DNA or RNA. In the present invention, the "nucleic acid fragment" may also comprise a modified nucleic acid or an artificial nucleic acid.

Alternatively, a nucleic acid fragment encoding a GABA transaminase protein with an N-terminally or C-terminally added amino acid sequence that has no influence on the enzyme activity can also be used. For example, a nucleic acid fragment consisting of a nucleotide sequence encoding a protein in which 1 to 50, for example, 1 to 33 amino acids are added to the N terminus of the GABA transaminase protein may be used as the GABA transaminase gene. Such an amino acid sequence that has no influence on the enzyme activity can be, for example, a selectable marker gene product or a reporter gene product, or a fragment thereof. Preferred examples thereof include β galactosidase-derived protein fragments (e.g., an amino acid sequence of positions 1 to 33 in SEQ ID NO: 6). The GABA transaminase protein comprising such an additional sequence is, for example, a protein consisting of the amino acid sequence shown by SEQ ID NO: 6. A nucleic acid fragment encoding such a protein is, for example, a nucleic acid fragment comprising the nucleotide sequence shown by SEQ ID NO: 5.

The GABA transaminase gene of the present invention can be isolated from an organism-derived nucleic acid by a conventional method on the basis of its nucleotide sequence (in the case of *Escherichia coli*, for example, the nucleotide sequence of SEQ ID NO: 1). For example, the GABA transaminase gene can be obtained as a DNA amplification fragment by PCR using a nucleic acid such as total mRNA prepared from an organism, for example, bacteria by a conventional method, cDNA obtained from total RNA by RT-PCR, or a cDNA library, as a template and a primer set designed on the basis of the sequence of the GABA transaminase gene. The obtained DNA amplification fragment can be extracted and purified by conventional methods. Alternatively, a probe is prepared using the GABA transaminase gene (e.g., DNA consisting of the nucleotide sequence of SEQ ID NO: 1) or a portion thereof and then the GABA transaminase gene can also be obtained as a clone by the hybridization of this probe to a nucleic acid such as total mRNA prepared from an organism, for example, bacteria by a conventional method, cDNA obtained from total RNA by RT-PCR, or a cDNA library. The GABA transaminase gene of the present invention may also be synthesized by a chemical synthesis method. Alternatively, the GABA transaminase gene may be prepared by the modification of a GABA transaminase gene isolated from a natural source or a synthesized GABA transaminase gene by a mutation method such as site-directed mutagenesis. The gene can be mutated by the adoption of an approach known in the art such as a Kunkel method or a Gapped duplex method, or a method equivalent thereto. Those skilled in the art can readily perform the gene mutation using, for example, a commercially available site-directed mutagenesis kit.

The sequence of the obtained nucleic acid fragment comprising the GABA transaminase gene is preferably verified by sequencing. The sequencing can be carried out by an approach known in the art such as a Maxam-Gilbert chemical modification method or a dideoxynucleotide chain termination method and can usually be carried out using an automatic sequencing apparatus (e.g., a DNA sequencer manufactured by Applied Biosystems, Inc. (ABI)).

In the present invention, the GABA transaminase gene is not intended to be included in a T-DNA region and to be thereby transferred to a plant genome. The gene is intended to be transferred to *Agrobacterium* so that the *Agrobacterium* retains the activity of the gene product and thereby exhibits improved (enhanced) gene transfer efficiency (gene transfer ability) to plants. In the present invention, therefore, the GABA transaminase gene is preferably transferred to *Agrobacterium* using a vector containing no T-DNA region. The T-DNA region refers to a region that is present in an extrachromosomal vector possessed by *Agrobacterium* and sandwiched between the right border sequence (RB) and left border sequence (LB). This region is cleaved from the vector during plant transformation with *Agrobacterium* and integrated into the plant genome. Specifically, the vector containing no T-DNA region, preferably used in the present invention, is not a vector (typically, a binary vector) having a T-DNA region that is insertable to the plant genome via *Agrobacterium*, but is an expression vector for inducing the expression of the gene of interest in *Agrobacterium*, a homologous recombination vector for integrating the gene of interest into the *Agrobacterium* genome, or the like. The vector used in the present invention is preferably a plasmid vector. The vector used in the present invention is also preferably a wide-host-range vector. Examples of the wide-host-range vector that can be preferably used in the present invention include, but are not limited to, pBBR1MCS-5, pBBR122, and RK2, and derivative strains thereof.

The GABA transaminase gene to be transferred to *Agrobacterium* is preferably located under the control of a promoter in a vector, preferably a vector containing no T-DNA region. In this context, the promoter used may be any promoter capable of functioning in bacteria, particularly, *Agrobacterium*, and may be any of constitutive promoters, inducible promoters, transient promoters, and organ-, tissue-, or cell-specific promoters. Examples of the promoter that can be preferably used to induce the expression of the GABA transaminase gene in *Agrobacterium* in the present invention include, but are not limited to, lac promoter, dnaK promoter, trp promoter, araB promoter, Pzt-1 promoter, recA promoter, lpp promoter, tac promoter, and vir promoter. Not only one copy but two or more copies of the GABA transaminase gene may be contained under the control of a promoter in a vector, preferably a vector containing no T-DNA region. In the present invention, when a plurality of genes are contained under the control of one promoter, these genes are preferably ligated in the same orientation at intervals short (e.g., 100 bp or less, preferably 50 bp or less) enough to undergo the control of the same promoter.

The *Agrobacterium* to which the GABA transaminase gene is transferred is not limited and may be any *Agrobacterium* species that can be used in the *Agrobacterium* method, such as *Agrobacterium tumefaciens*, *Agrobacterium vitis*, *Agrobacterium rhizogenes*, or *Agrobacterium radiobacter*. Specifically, for example, an *Agrobacterium tumefaciens* GV2260, an *Agrobacterium tumefaciens* C58 strain, an *Agrobacterium vitis* S4 strain, an *Agrobacterium rhizogenes* A4 strain, or an *Agrobacterium radiobacter* K84 strain, or a derivative strain thereof, or any of other *Agrobacterium* strains for use in plant transformation can be preferably used. Examples thereof include, but are not limited to, GV2260, C58C1RifR, GV3850, GV3101, EHA101, EHA105, AGL1, LBA4404, and K84N6 strains. For use in plant transformation, *Agrobacterium* having a vector or genomic region comprising a vir region involved in gene transfer to plant cells (typically, a helper plasmid having the vir region) is preferred.

The vector comprising the GABA transaminase gene can typically be transferred to the *Agrobacterium* by, but not limited to, electroporation. The vector-introduced *Agrobacterium* can be cultured in, for example, a selection medium containing an antibiotic or the like corresponding to a selectable marker such as a drug resistance gene contained in the vector to select a transformed *Agrobacterium*. The selected transformed *Agrobacterium* may be cultured in a selection medium so that the transformed *Agrobacterium* maintains the introduced GABA transaminase gene.

The introduced GABA transaminase gene may be maintained extrachromosomally in a vector form (i.e., in a state contained in a vector such as a plasmid) in the obtained transformed *Agrobacterium* or may be integrated into the genome of the *Agrobacterium* and thereby harbored. In the case of transferring the GABA transaminase gene to the *Agrobacterium* using an expression vector, the GABA transaminase gene is preferably harbored in a state contained in the autonomously replicating expression vector so as to express the GABA transaminase protein. In the case of transferring the GABA transaminase gene to the *Agrobacterium* using a homologous recombination vector targeting the *Agrobacterium* genome, the GABA transaminase gene is preferably harbored in a state integrated in the genome so as to express the GABA transaminase protein. In the present invention, an *Agrobacterium* bacterium harboring the introduced GABA transaminase gene or its progeny *Agrobacterium* bacterium which can exhibit GABA transaminase activity is referred to as the transformed *Agrobacterium* according to the present invention.

In the present invention, a foreign ACC deaminase gene is also preferably transferred to the *Agrobacterium*, in addition to the GABA transaminase gene. In the present invention, the "foreign" ACC deaminase gene refers to an ACC deaminase gene exogenously introduced into an *Agrobacterium* bacterium, or an ACC deaminase gene maintained in the progeny of the *Agrobacterium* bacterium. The ACC deaminase gene used in the present invention encodes an ACC deaminase. The ACC deaminase degrades an ethylene biosynthesis intermediate ACC (1-aminocyclopropane-1-carboxylate) into α-ketobutyrate and ammonia and can thereby inhibit intracellular ethylene production. Plants produce ethylene as a protective action against pathogens, and ethylene has the effect of inhibiting the expression of vir gene in the *Agrobacterium*. In this respect, the inhibition of the expression of vir gene in the *Agrobacterium* is canceled by the inhibition of ethylene production through the action of the ACC deaminase. As a result, the *Agrobacterium*-mediated gene transfer efficiency to cells can be further enhanced. The ethylene production is a defensive response mechanism common to a wide range of plants.

The ACC deaminase gene used in the present invention may be a gene that is derived from any organism species and encodes an enzyme having ACC-degrading activity. For example, an ACC deaminase gene derived from a soil microorganism including a bacterium such as a bacterium of the genus *Pseudomonas* (*Pseudomonas* sp. ACP strain, *Pseudomonas fluorescens*, *Pseudomonas putida*, *Pseudomonas stutzeri*, *Pseudomonas entomophila* PS-PJH strain, etc.), a bacterium of the genus *Pannonibacter* (*Pannonibacter phragmatetus* PB-Rt1., etc.), a bacterium of the genus *Enterobacter* (*Enterobacter cloacae* LH-R2, etc.), a bacterium of the genus *Rhizobium* (*Rhizobium* sp. QR1, etc.), a bacterium of the genus *Achromobacter* (*Achromobacter* sp., etc.), a bacterium of the genus *Sinorhizobium* (*Sinorhizobium* sp. BL3 strain, etc.), or a bacterium of the genus *Mesorhizobium* (*Mesorhizobium loti*, etc.) can be preferably used. As an example of the ACC deaminase gene suitable for the combined use with the GABA transaminase gene, for example, a nucleic acid fragment comprising a nucleotide sequence encoding the amino acid sequence shown by SEQ ID NO: 14, for example, derived from a *Pseudomonas* sp. ACP strain, for example, a nucleic acid fragment having the nucleotide sequence shown by SEQ ID NO: 13 as an open reading frame (ORF), may be used as the ACC deaminase gene. Alternatively, a nucleic acid fragment consisting of a nucleotide sequence having 70% or more, preferably 80% or more, preferably 85% or more, more preferably 90% or more, for example, 95%, 98%, or 99% or more sequence identity to the nucleotide sequence (full length) shown by SEQ ID NO: 13 and encoding a protein having ACC deaminase activity may be used as the ACC deaminase gene. Also, a nucleic acid fragment consisting of a nucleotide sequence encoding a protein that consists of an amino acid sequence derived from the amino acid sequence shown by SEQ ID NO: 14 by the deletion, substitution, or addition of 1 to 50, preferably 1 to 10, for example, 1 to 5 amino acids and has ACC deaminase activity may be used as the ACC deaminase gene. In addition, a nucleic acid fragment consisting of a nucleotide sequence encoding a protein that consists of an amino acid sequence having 70% or more, preferably 80% or more, preferably 85% or more, more preferably 90% or more, for example, 95%, 98%, or 99% or more sequence identity to the amino acid sequence (full length) shown by SEQ ID NO: 14 and has ACC deaminase activity may be used as the ACC deaminase gene. The ACC deaminase activity can be determined by use of an ACC deaminase activity measurement method known in the art. Specifically, for example, 1-aminocyclopropane-carboxylic acid (ACC) and pyridoxal-5'-phosphate (PLP) are added to a solution of the protein having ACC deaminase activity, and the mixture is incubated at 30° C. Then, the reaction is terminated by the addition of a 100% (w/v) trichloroacetic acid (TCA) solution to the reaction solution. A 0.1% 2,4-dinitrophenylhydrazine (DNPH) solution is added thereto in an amount equivalent to the reaction solution, and the mixture is incubated at 30° C. for 15 minutes, and then a coloring reaction is terminated by the addition of a 3 N sodium hydroxide solution in an amount equivalent to the reaction solution. α-ketobutyrate accumulated in the coloring reaction solution is detected at an absorption wavelength of 340 nm. The α-ketobutyrate is produced from 1-aminocyclopropane-carboxylate (ACC) by the catalytic action of the ACC deaminase. Thus, if the amount of the α-ketobutyrate accumulated is shown to be increased with increase in the amount of the protein, it can be concluded that the ACC deaminase activity has been determined. Alternatively, a nucleic acid fragment encoding an ACC deaminase protein with an N-terminally or C-terminally added amino acid sequence that has no influence on the enzyme activity may be used. For example, a nucleic acid fragment consisting of a nucleotide sequence encoding a protein in which 1 to 50, for example, 1 to 33 amino acids are added to the N terminus of the ACC deaminase protein may be used as the ACC deaminase gene. Such an amino acid sequence that has no influence on the enzyme activity can be, for example, a selectable marker gene product or a reporter gene product, or a fragment thereof. Preferred examples thereof include β galactosidase-derived protein fragments (e.g., an amino acid sequence of positions 1 to 33 in SEQ ID NO: 6). The ACC deaminase gene can be obtained according to the aforementioned method for obtaining the GABA transaminase gene.

The ACC deaminase gene to be transferred to the *Agrobacterium* is preferably located under the control of a promoter in a vector, preferably a vector containing no T-DNA region. Any of the promoters mentioned above in relation to the GABA transaminase gene can be preferably used as the promoter. One copy or two or more copies of the ACC deaminase gene may be contained under the control of the promoter. This is also as mentioned above in relation to the GABA transaminase gene.

The introduced ACC deaminase gene may be maintained extrachromosomally in a vector form (i.e., in a state contained in a vector such as a plasmid) in the obtained transformed *Agrobacterium* so as to express the ACC deaminase protein or may be integrated into the genome of the *Agrobacterium* and thereby harbored so as to express the ACC deaminase protein.

In the present invention, the GABA transaminase gene and the ACC deaminase gene may be respectively contained in separate vectors for transfer to the *Agrobacterium*. Alternatively, the GABA transaminase gene and the ACC deaminase gene may be contained in a single vector for transfer. In the case of transferring these two genes contained in a single vector, these genes may be located in tandem under the control of one promoter, but more preferably, each promoter is located upstream of each of the genes. These promoters may be the same as or different from each other. Preferably, lac promoter is used as both of these promoters.

The ACC deaminase gene can be transferred to the *Agrobacterium* in the same way as the aforementioned method for transferring the GABA transaminase gene to the *Agrobacterium*.

The GABA transaminase gene and/or the ACC deaminase gene are preferably contained, together with one or two or more additional foreign gene(s) such as a marker gene, in the vector for transfer to the *Agrobacterium*. The GABA transaminase gene and the ACC deaminase gene are preferably located upstream than the additional foreign gene in the vector. A drug resistance gene such as a gentamicin resistance gene, a neomycin resistance gene, a hygromycin resistance gene, a puromycin resistance gene, a Zeocin resistance gene, a Blasticidin resistance gene, a dihydrofolate reductase gene, or an ampicillin resistance gene can be preferably used as the marker gene. A reporter gene such as a gene encoding a fluorescent protein may be used. Alternatively, a sequence that allows *Agrobacterium* cells to stably harbor plasmids (e.g., a gene sta sequence involved in plasmid stabilization) may be contained as the additional foreign gene in the vector comprising the GABA transaminase gene and/or the ACC deaminase gene. In the present invention, the "additional foreign gene" means a gene other than the GABA transaminase gene and the ACC deaminase gene wherein the gene encodes a protein or functional RNA and is not naturally possessed by the host *Agrobacterium*. When the additional foreign gene is contained together with the GABA transaminase gene and/or the ACC deaminase gene in the vector, a transcription termination sequence is preferably located between the GABA transaminase gene and/or the ACC deaminase gene and the additional foreign gene.

The transcription termination sequence is not particularly limited as long as this sequence is capable of functioning as signals for mRNA transcription termination. For example, a transcription termination sequence naturally present downstream of each gene may be used, or a transcription termination sequence present downstream of any known gene may be prepared by PCR amplification or the like and used. Specific examples thereof include the transcription termination sequence of an ampicillin drug resistance gene. Examples of the transcription termination sequence of the ampicillin drug resistance gene include the nucleotide sequence shown by SEQ ID NO: 12 and a nucleotide sequence having 80% or more, preferably 90% or more, more preferably 95% or more, for example, 98% or 99% or more sequence identity to the sequence of SEQ ID NO: 12 and having terminator activity.

The obtained transformed *Agrobacterium* can be used to carry out gene transfer to a plant with high efficiency. This gene transfer to a plant using the transformed *Agrobacterium* according to the present invention can be carried out according to the procedures of the conventional *Agrobacterium* method. Specifically, for example, any gene (a gene of interest) to be transferred to a plant is integrated under the control of a promoter and a terminator to between the right border sequence (RB) and the left border sequence (LB) of a vector such as a plasmid (typically, a binary vector) for plant transformation containing a T-DNA region. This vector can be transferred to the transformed *Agrobacterium* according to the present invention by a conventional method and used in gene transfer to the plant. The marker gene as mentioned above may be integrated, together with the gene of interest, within the T-DNA region. The present invention also provides a transformed *Agrobacterium* comprising the vector comprising the GABA transaminase gene and/or the ACC deaminase gene as well as a vector comprising a T-DNA region (preferably a binary vector comprising a T-DNA region) having an insert of the gene of interest. Examples of the binary vector comprising a T-DNA region include a large number of T-DNA binary vectors known in the art such as pIG121-Hm, pEKH$_2$, pRI 909, pRI 910, and BIBAC1 (see e.g., Lee, L. Y and Gelvin, S. B. (2008) T-DNA Binary Vectors and Systems, Pant Physiology 146: 325-332). The vector pIG121-Hm has a GUS gene located under the control of 35S promoter in the T-DNA region, while the vector pEKH$_2$ has a GUS gene under the control of corn-derived Ubi promoter in the T-DNA region. The transformed *Agrobacterium* according to the present invention is required to harbor a vir region involved in gene transfer to plant cells, in an expressible form. For this purpose, if necessary, a helper vector having the vir region may be further transferred thereto. In a preferred embodiment, in the vector-introduced, transformed *Agrobacterium* according to the present invention, the vector comprising the GABA transaminase gene and/or the ACC deaminase gene, the helper vector having the vir region, and the binary vector having the T-DNA region comprising the gene to be transferred to a plant coexist with each other. Alternatively, the GABA transaminase gene and/or the ACC deaminase gene may be integrated into the helper vector having the vir region in the *Agrobacterium*.

Subsequently, the resulting transformed *Agrobacterium* is inoculated to, for example, plant tissues, plant cells (calli, etc.), or seeds and allowed to infect them by cocultivation to insert the T-DNA region into the genome in the plant cells. The cocultivation medium for use in the cocultivation is not particularly limited, but is also preferably a medium based on an MS medium. The cocultivation medium preferably contains acetosyringone (e.g., 50 µM to 500 µM, as a preferred example, 100 µM to 300 µM) and glucose (e.g., 0.5 to 10%, as a preferred example, 1 to 5%).

The *Agrobacterium*-mediated transformation method using the transformed *Agrobacterium* of the present invention can be carried out for any plant that can be infected by *Agrobacterium*. The plant to be transformed with the *Agrobacterium* according to the present invention may be, for example, a dicotyledon or a monocotyledon. Examples of the plant include, but are not particularly limited to, plants of the family Solanaceae [eggplant (*Solanum melongena* L.), tomato (*Solanum lycopersicum*), bell pepper (*Capsicum annuum* L. var. *angulosum* Mill.), chili pepper (*Capsicum annuum* L.), tobacco (*Nicotiana tabacum* L.), etc.], the family Poaceae [rice (*Oryza sativa*), wheat (*Triticum aestivum* L.), barley (*Hordeum vulgare* L.), corn (*Zea mays* L.), sorghum (*Sorghum bicolor* (L.) Moench), erianthus (*Erianthus ravennae*), Guinea grass (*Panicum maximum* Jacq.), miscanthus (*Miscanthus* spp.), sugarcane (*Saccharum officinarum* L.), Napier grass (*Pennisetum purpureum* Schumach), pampas grass (*Cortaderia argentea* Stapf), perennial ryegrass (*Lolium perenne* L.), Italian ryegrass (*Lolium multiflorum* Lam.), meadow fescue (*Festuca pratensis* Huds.), tall fescue (*Festuca arundinacea* Schreb.), orchard grass (*Dactylis glomerata* L.), timothy (*Phleum pratense* L.), etc.], the family Brassicaceae [thale cress (*Arabidopsis thaliana*), turnip rape (*Brassica campestris* L.), Chinese cabbage (*Brassica pekinensis* Rupr.), cabbage (*Brassica oleracea* L. var. *capitata* L.), radish (*Raphanus sativus* L.), rapeseed (*Brassica campestris* L. and *B. napus* L.), etc.], the family Leguminosae [soybean (*Glycine max*), adzuki bean (*Vigna angularis* Willd.), common bean (*Phaseolus vulgaris* L.), broad bean (*Vicia faba* L.), etc.], the family Cucurbitaceae [cucumber (*Cucumis sativus* L.), melon (*Cucumis melo* L.), watermelon (*Citrullus vulgaris* Schrad.), pumpkin (*C. moschata* Duch. and *C. maxima* Duch.), etc.], the family Convolvulaceae [sweetpotato (*Ipomoea batatas*), etc.], the family Liliaceae [leek (*Allium fistulosum* L.), onion (*Allium cepa* L.), Chinese chive (*Allium tuberosum* Rottl.), garlic (*Allium sativum* L.), asparagus (*Asparagus officinalis* L.), etc.], the family Lamiaceae [perilla (*Perilla frutescens* Britt. var. *crispa*), etc.], the family Compositae [Hardy garden mum (*Chrysanthemum morifolium*), chop-suey green (*Chrysanthemum coronarium* L.), lettuce (*Lactuca sativa* L. var. *capitata* L.), etc.], the family Rosaceae [rose (*Rosa hybrida* Hort.), strawberry (*Fragaria×ananassa* Duch.), etc.], the family Rutaceae [satsuma mandarin (*Citrus unshiu*), Szechuan pepper (*Zanthoxylum piperitum* DC.), etc.], the family Myrtaceae [eucalyptus (*Eucalyptus globulus* Labill), etc.], the family Salicaceae [poplar (*Populus nigra* L. var. *italica* Koehne), etc.], the family Chenopodiaceae [spinach (*Spinacia oleracea* L.), beet (*Beta vulgaris* L.), etc.], the family Gentianaceae [Japanese gentian (*Gentiana scabra* Bunge var. *buergeri* Maxim.), etc.], and the family Caryophyllaceae [carnation (*Dianthus caryophyllus* L.), etc.]. A plant of the family Poaceae as the monocotyledon or a plant of the family Solanaceae as the dicotyledon is particularly preferred for the transformation of the present invention, though the plant of the present invention is not limited thereto.

The plant tissues, the plant cells (calli, etc.), the seeds, or the like, having the gene of interest integrated in the genome via the *Agrobacterium* according to the present invention, can be regenerated into a plant body by a method known in the art. For example, the transformed plant cells having the integrated gene of interest are cultured in a selection medium according to a conventionally known plant tissue culture method, and survived calli can be cultured in a redifferentiation medium (containing an appropriate concentration of a plant hormone such as auxin, cytokinin, gibberellin, abscisic acid, ethylene, brassinolide, or the like) to regenerate a transformed plant body (particularly, shoot). Examples of the cytokinin include zeatin. The regenerated plant body can be further transplanted to a rooting medium and allowed to grow.

The presence or absence of the insertion of the gene of interest into the plant genome can be determined by testing transformants for the activity of the gene product from the gene of interest or by testing transformants for the activity of the marker gene product in the case that the marker gene has been integrated together with the gene of interest into the plant genome. Alternatively, the gene of interest and/or the marker gene integrated into the genome can be specifically amplified by PCR and sequenced to verify the presence or absence of the insertion more securely. Concerning the transformed plant bodies, the insertion of the gene of interest into the genome is preferably determined for diploid individuals among plant bodies shown a rooting on a rooting medium.

For the details of the plant transformation method, see the description of general textbooks such as "Ko Shimamoto and Kiyotaka Okada (editorial supervisors) "New edition, Experimental protocol for model plant, From genetic technique to genome analysis" (2001), Shujunsha Co., Ltd." or literatures such as Hiei Y. et al., "Efficient transformation of rice (*Oryza sativa* L.) mediated by *Agrobacterium* and sequence analysis of the boundaries of the T-DNA." Plant J. (1994) 6, 271-282; and Hayashimoto, A. et al., "A polyethylene glycol-mediated protoplast transformation system for production of fertile transgenic rice plants." Plant Physiol. (1990) 93, 857-863.

In the present invention, the *Agrobacterium*-mediated transformation can be carried out using the transformed *Agrobacterium* harboring the introduced GABA transaminase gene to improve gene transfer efficiency to host organisms, typically, plants, as compared with when using an *Agrobacterium* equivalent thereto except that this *Agrobacterium* has not been transfected with a GABA transaminase gene. In the present invention, the gene transfer efficiency refers to a ratio of the number of host explants or host cells exhibiting phenotypes resulting from the gene transfer to the number of host explants or host cells subjected to the contact with the *Agrobacterium*. In the present invention, the gene transfer efficiency can also be expressed as a ratio of the number of transformed individuals determined to have successful gene transfer to the genome to the number of host explants subjected to the contact with the *Agrobacterium*. The gene transfer efficiency can be evaluated by use of an approach differing depending on the type of the transferred gene of interest or marker gene, but can be basically evaluated according to the description of Examples 6 to 8. The level of improvement in the gene transfer efficiency is not limited and can be, for example, 10% or more, preferably 20% or more, more preferably 50% or more, further preferably 100% or more, particularly, 200% or more improvement. In the present invention, the transformed *Agrobacterium* harboring the GABA transaminase gene introduced as mentioned above can be used in the *Agrobacterium*-mediated transformation (gene transfer) method to transfer the gene of interest to plant cells with significantly high efficiency and efficiently produce transformed plants. In the present invention, the transformed *Agrobacterium* harboring the GABA transaminase gene and the ACC deaminase gene introduced together can also be used to transfer the gene of interest to plant cells with higher efficiency.

The present invention, as also shown in Examples, can significantly improve the gene transfer efficiency even if the existing transformation method (Patent Literature 1) which involves transferring the ACC deaminase gene alone to *Agrobacterium* is not sufficiently effective depending on the type of a plant such as *erianthus*. In the present invention, the mere transfer of the GABA transaminase gene alone to *Agrobacterium* largely improves the gene transfer efficiency, whereas the transfer of the GABA transaminase gene and the ACC deaminase gene in combination can further improve the gene transfer efficiency.

Plants also secrete various substances other than ethylene when infected by *Agrobacterium*, for inhibition of *Agrobacterium*-mediated gene transfer. Depending on the type of a plant, therefore, it is considered that the gene transfer efficiency may not be sufficiently enhanced by the mere inhibition of ethylene production. Ethylene and GABA differ in the mechanism to inhibit gene transfer. This suggests that the inhibition of GABA by the GABA transaminase gene product brings about remarkable effects on even the type of the plant on which the mere inhibition of ethylene production is not sufficient for exerting the effect. A GABA metabolite succinic semialdehyde has also been reported to inhibit the quorum sensing signals of *Agrobacterium* (Wang et al., 2006 Molecular Microbiology 62: 45-56). Hence, it was assumed, in the course of the development of the transformed *Agrobacterium* according to the present invention, that succinic semialdehyde might inhibit the gene transfer through the metabolism of GABA by the GABA transaminase. Surprisingly, the present inventors have showed that the gene transfer efficiency can be largely improved without being significantly inhibited by the GABA metabolite, by imparting GABA transaminase activity to the *Agrobacterium*. The present invention also provides such a method for producing a transformed plant.

EXAMPLES

Hereinafter, the technique of the present invention will be described further specifically with reference to Examples. However, the technical scope of the technique of the present invention is not intended to be limited by these Examples.

[Example 1] Cloning and Sequence Analysis of GABA Transaminase Gene

In this Example, a GABA transaminase gene was cloned from an *Escherichia coli* K12 strain. First, the *Escherichia coli* K12 strain was proliferated and maintained in an LB medium at 37° C. Total DNA was extracted from the *E. coli* K12 strain by the method of Sambrook et al. (2001) for use as a template for PCR. On the basis of the genome information of this strain (http://www.ncbi.nlm.nih.gov/nuccore/NC_010473.1, NCBI GenBank database), two primers gabTF (5'-aagcttaatgaacagcaataaagagtt-3' (SEQ ID NO: 3)) and gabTR (5'-tctagactactgcttcgcctcatcaaaac-3' (SEQ ID NO: 4)) for the cloning of the GABA transaminase (gabT) gene were designed and synthesized. PCR was carried out using the extracted total DNA and these primers under the following conditions: thermal denaturation at 94° C. for 2 minutes followed by 35 repetitive temperature cycles each involving 94° C. for 45 seconds, 58° C. for 45 seconds, and 72° C. for 2 minutes. The PCR product having the expected size (1294 bp) (gabT fragment 1) was cloned into a cloning vector pET-21b(+) (Promega, USA) (pETgabT) (FIG. 1). The cloned DNA fragment was sequenced using a DNA sequencer ABI310 and DNA Sequencing Kit Big Dye Terminator cycle sequencing Ready Reaction (Applied Biosystems, Tokyo) and thereby verified to have a sequence identical to the registered sequence on the GenBank database (Accession No. NC_010473.1, Gene ID: 6061113, gabT). The nucleotide sequence of the open reading frame (ORF) of the GABA transaminase gene gabT contained in the obtained cloned DNA is shown in SEQ ID NO: 1, and the amino acid sequence of the GABA transaminase protein encoded by the nucleotide sequence is shown in SEQ ID NO: 2.

[Example 2] Construction of gabT Expression Vector

Figure 2:
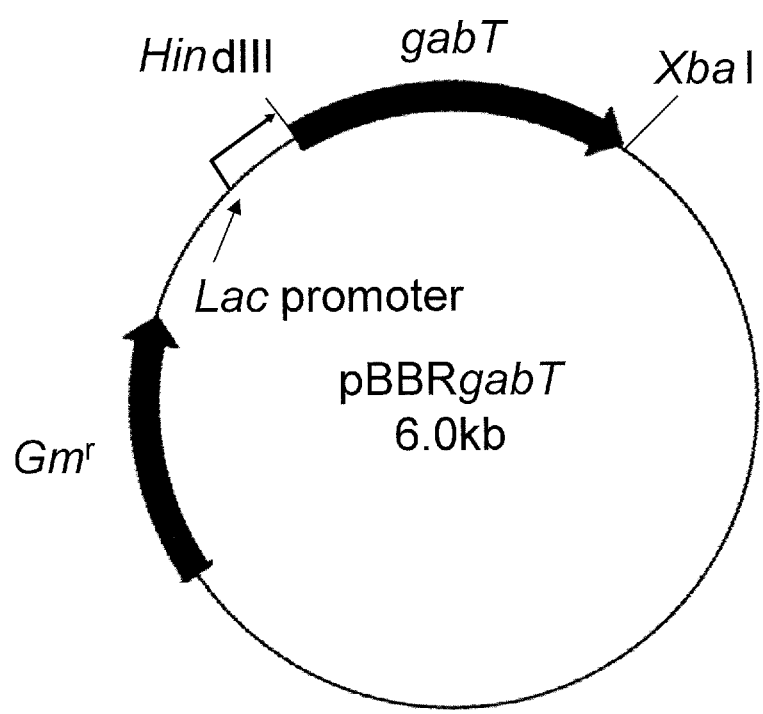
FIG. 2 shows a plasmid map of an expression vector pBBRgabT having a GABA transaminase gene.

The plasmid pETgabT was extracted according to a conventional method from the recombinant *E. coli* DH5α (pETgabT) obtained in Example 1. The GABA transaminase gene (gabT) was cleaved with restriction enzymes HindIII and XbaI and subcloned into the multicloning site of a wide-host-range vector pBBR1MCS-5 (Kovach et al., 1995, Gene 166, 175-176) (pBBRgabT, FIG. 2). The GABA transaminase protein expressed from this recombinant plasmid has N-terminally added β galactosidase-derived 33 amino acids encoded by a sequence (lacZ gene fragment) in pBBR1MCS-5 (FIG. 3, nucleotide sequence: SEQ ID NO: 5, amino acid sequence: SEQ ID NO: 6). The N-terminally added β galactosidase-derived 33 amino acids have no influence on the activity of the GABA transaminase. The expression of the gabT gene is placed under the control of lac promoter on this plasmid.

[Example 3] Construction of Expression Vector for Coexpression of GABA Transaminase Gene and ACC Deaminase Gene A DNA fragment containing the GABA transaminase gene (gabT) was amplified by PCR using the pBBRgabT expression vector prepared in Example 2 as a template and primers acdS-for (5'-tctgcgcgtaatctgctgcttgagcgcaacgcaattaatg-3'(SEQ ID NO: 7)) and gabT-Rev (5'-cgattctagactactgcttcgcctcatcaaaac-3' (SEQ ID NO: 8)). The obtained amplification fragment (gabT fragment 2; SEQ ID NO: 9) contained a 5'-noncoding region containing the lac promoter (including a ribosomal binding sequence), and a sequence encoding the GABA-transaminase protein with the N-terminally added β galactosidase-derived 33 amino acids (FIG. 4).

Next, a DNA fragment containing the transcription termination region of an ampicillin drug resistance gene was amplified by PCR using a pUC18 vector as a template and two primers amp_ter-for2 (5'-GCTAGAATTCCTGTCAGACCAAGTTTACTC-3' (SEQ ID NO: 10)) and amp_ter-rev2 (5'-CATTAATTGCGTTGCGCTCAAGCAGCAGATTACGCGCAGA-3' (SEQ ID NO: 11)). The nucleotide sequence of the obtained amplification fragment (amp-term fragment) is shown in SEQ ID NO: 12.

The two amplification fragments thus obtained, i.e., the gabT fragment 2 and the amp-term fragment, were ligated by fusion PCR using primers amp_ter-for2 and gabT-Rev. The obtained PCR product was digested with restriction enzymes EcoRI and XbaI.

Figure 5:
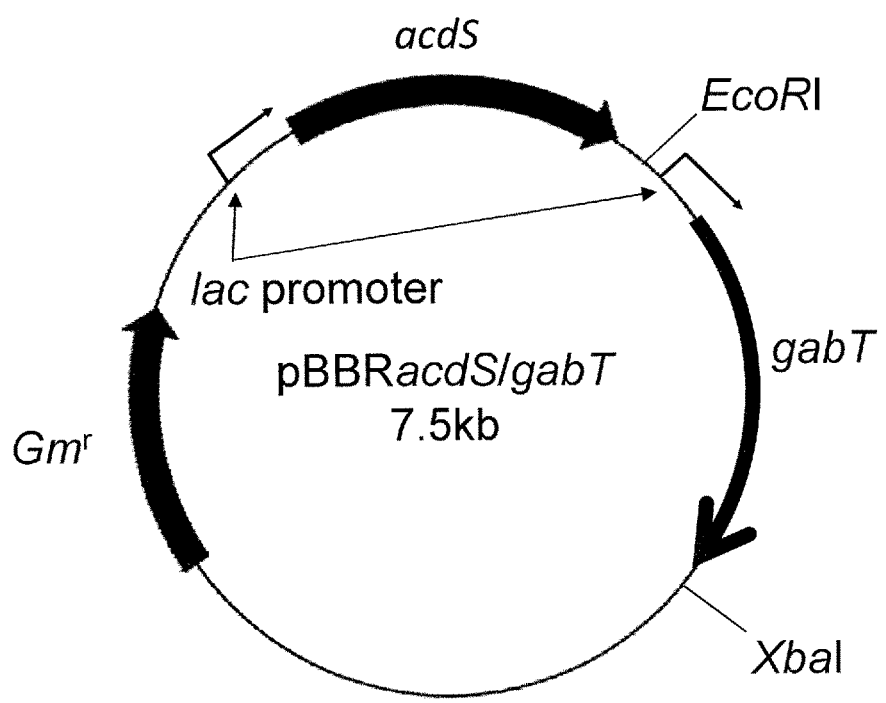
FIG. 5 shows a plasmid map of a vector pBBRacdS/gabT for the co-expression of ACC deaminase gene and GABA transaminase gene.

Subsequently, the obtained EcoRI-XbaI digestion fragment was ligated with a *Pseudomonas* ACC deaminase expression vector pBBRacdS (Nonaka et al., Appl. Environ. Microbiol., 74, 2526-2528 (2008)) digested with restriction enzymes EcoRI and XbaI, and the ligation product was cloned in *Escherichia coli* DH5α to prepare an expression vector for the coexpression of the GABA transaminase gene and the ACC deaminase gene (pBBRacdS/gabT) (FIG. 5). The nucleotide sequence of the ACC deaminase gene is shown in SEQ ID NO: 13, and the amino acid sequence of the ACC deaminase protein encoded by the nucleotide sequence is shown in SEQ ID NO: 14.

[Example 4] Gene Transfer to *Agrobacterium*

The plasmid vector pBBRgabT constructed in Example 2 and the plasmid vector pBBRacdS/gabT constructed in Example 3 were each transferred by electroporation to an *Agrobacterium* strain *Agrobacterium tumefaciens* GV2260 harboring a binary plasmid pIG121-Hm or an *Agrobacterium* strain *Agrobacterium tumefaciens* GV2260 harboring a binary plasmid pEKH$_2$. These GV2260 strains have a helper plasmid having a vir region. Their binary plasmids have a GUS (uidA) gene insert, which can be used as an indicator for gene transfer to plants. The *Agrobacterium* strain GV2260(pBBRgabT, pIG121-Hm), the *Agrobacterium* strain GV2260(pBBRgabT, pEKH$_2$), the *Agrobacterium* strain GV2260(pBBRacdS/gabT, pIG121-Hm), and the *Agrobacterium* strain GV2260(pBBRacdS/gabT, pEKH$_2$) each harboring the introduced vector were obtained by culture and maintenance in an LB medium containing antibiotics, i.e., 50 mg/L gentamicin, 100 mg/L kanamycin, and 100 mg/L ampicillin or an LB medium containing 50 mg/L gentamicin, 50 mg/L spectinomycin, and 100 mg/L ampicillin.

An *Agrobacterium* concurrently harboring the two plasmids was verified by direct PCR using its colony as a template. The gabT gene was detected using primers gabTF and gabTR, and the uidA gene was detected using primers GUSF (5'-atccacgccgtattcgg-3' (SEQ ID NO: 15)) and GUSR (5'-catgaagatgcggacttacg-3' (SEQ ID NO: 16)).

Also, an *Agrobacterium* strain GV2260(pBBR1MCS-5, pIG121-Hm) and an *Agrobacterium* strain GV2260 (pBBR1MCS-5, pEKH$_2$) harboring a plasmid vector pBBR1MCS-5 free from the gabT gene were obtained as controls in the same way as above except that the plasmid vector pBBR1MCS-5 was transferred thereto.

In addition, an *Agrobacterium* strain GV2260(pBBRacdS, pIG121-Hm) harboring an ACC deaminase gene-expressing plasmid vector pBBRacdS was obtained in the same way as above except that the plasmid vector pBBRacdS was transferred thereto.

[Example 5] Measurement of GABA Transaminase Activity

The gabT activity was measured for the *Agrobacterium* strain GV2260(pBBRgabT, pEKH$_2$) and the *Agrobacterium* strain GV2260(pBBRacdS/gabT, pEKH$_2$) prepared in Example 4. The gabT activity of the control *Agrobacterium* strain GV2260(pBBR1MCS-5, pEKH$_2$) was also measured. These *Agrobacterium* strains were each cultured in an LB medium containing 50 mg/L gentamicin, 50 mg/L spectinomycin, and 100 mg/L ampicillin. After 22 hours into the culture, the *Agrobacterium* cells (O.D. 600=0.8) were collected and lysed using a bacterium-derived protein extraction reagent BugBuster Master mix (Novagen). A protease inhibitor (Protease Inhibitor Cocktail set II, Novagen) was added to the lysate, and mixed with rotation at room temperature for 20 minutes. Then, the mixture was centrifuged at 16,000×g for 20 minutes, and the supernatant was transferred to a new tube. Subsequently, the protein concentration in the supernatant was measured using a protein assay kit (BCA Protein Assay kit, Novagen). Further, 100 ng of the supernatant (crude enzyme protein extract) was added to a reaction solution (0.1 M Bicine-NaOH, 0.1 M pyridoxal phosphate, 10 mM 2-ketoglutarate, and 10 mM GABA) to cause GABA transaminase reaction. This enzyme reaction was carried out at 37° C., and the reaction time was set to 0 minutes, 10 minutes, 20 minutes, 30 minutes, 60 minutes, 120 minutes, and 180 minutes.

After the enzyme reaction, the amount of the reaction product glutamate was measured using YAMASA L-Glutamate Assay Kit II (Yamasa Corp.). In this measurement, the reaction product glutamate is oxidized by L-glutamate oxidase included in the kit to produce hydrogen peroxide, which in turn produces a blue dye through peroxidase reaction. This blue dye is measured at a wavelength of 600 nm to measure the amount of the glutamate in the reaction solution.

Figure 6:
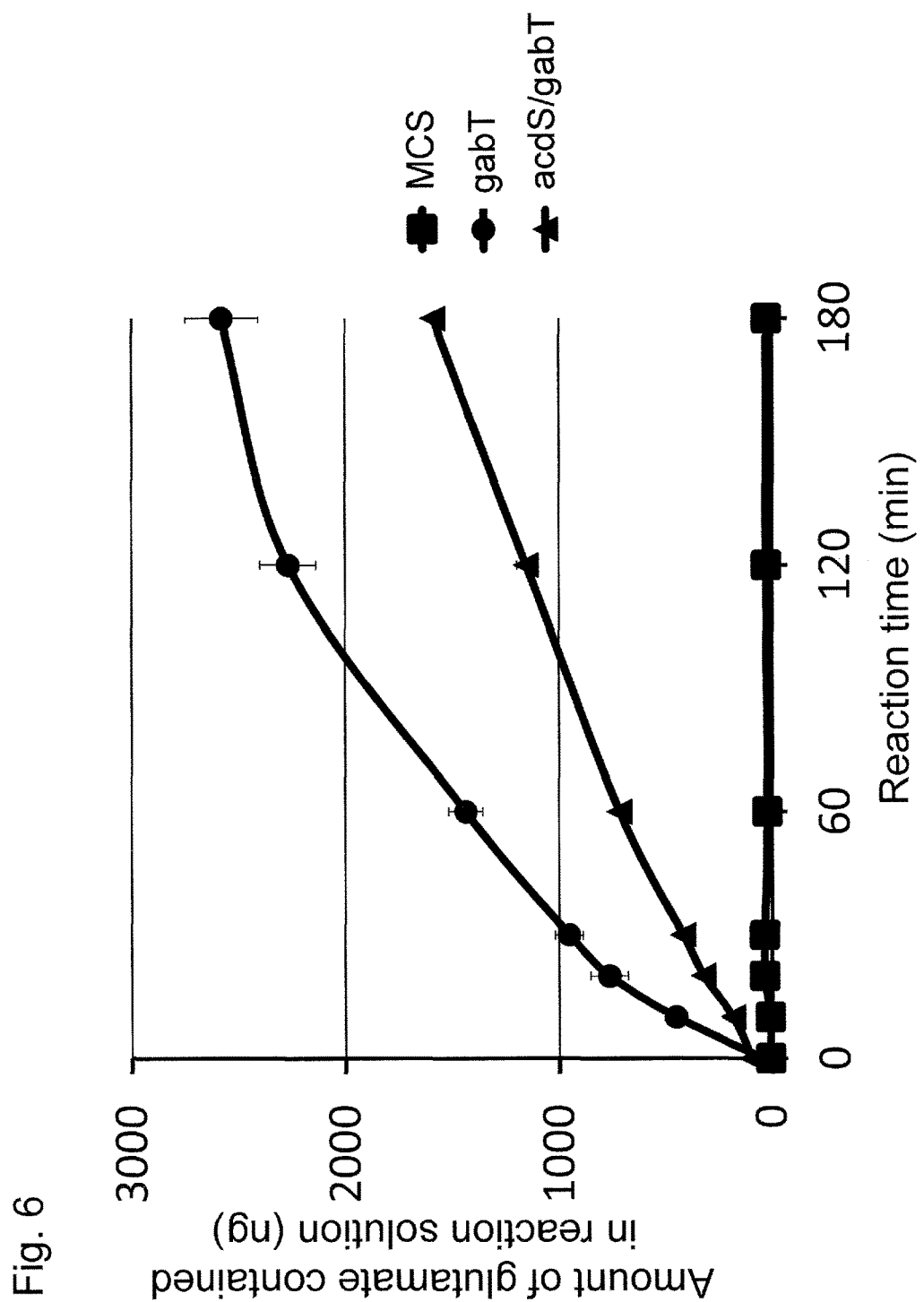
FIG. 6 shows results of measuring gabT enzyme activity in *Agrobacterium*. MCS: *Agrobacterium* strain GV2260 (pBBR1MCS-5, pEKH$_2$); gabT: *Agrobacterium* strain GV2260 (pBBRgabT, pEKH$_2$); and acdS/gabT: *Agrobacterium* strain GV2260 (pBBRacdS/gabT, pEKH$_2$). n=3. The error bar indicates standard deviation.

As a result of the enzyme reaction, a larger amount of the reaction product glutamate was measured in the case of using the crude enzyme extracts obtained from the *Agrobacterium* strain GV2260(pBBRgabT, pEKH$_2$) and the *Agrobacterium* strain GV2260(pBBRacdS/gabT, pEKH$_2$) than in the case of using the crude enzyme extract derived from the control *Agrobacterium* strain GV2260 (pBBR1MCS-5, pEKH$_2$), and this difference in the amount of the glutamate was shown to be increased with increase in the reaction time (FIG. 6). This indicates that the *Escherichia coli*-derived GABA transaminase is stably expressed from the vector transferred to the *Agrobacterium* and has activity in the *Agrobacterium*. These results demonstrated that the transfer of the GABA transaminase gene to the *Agrobacterium* can impart the GABA transaminase activity to the *Agrobacterium*.

[Example 6] Evaluation of Gene Transfer Efficiency to Plant-1

The *Agrobacterium* strain GV2260(pBBRgabT, pIG121-Hm), the *Agrobacterium* strain GV2260(pBBRgabT, pEKH$_2$), and the *Agrobacterium* strain GV2260 (pBBRacdS/gabT, pEKH$_2$) harboring the introduced GABA transaminase gene were evaluated for their gene transfer ability to plants. In this context, the gene to be transferred to plants was a GUS gene that is contained in the T-DNA regions of the binary vectors pIG121-Hm and pEKH$_2$ and used as a marker for gene transfer to plants (Hiei et al., Plant J., 6 (2): 271-282 (1994)).

First, the *Agrobacterium* strain GV2260(pBBRgabT, pIG121-Hm) and the control *Agrobacterium* strain GV2260 (pBBR1MCS-5, pIG121-Hm) were each used to evaluate the transfer efficiency of the GUS gene to a dicotyledon tomato (*Solanum lycopersicum* 'Money Maker'). Tomato seeds were aseptically inoculated on ½ MS (Murashige-Skoog) medium containing 1.5% sucrose and allowed to grow. The upper and lower regions of the obtained cotyledons were cut off, and evenly divided sections were used as tomato explants. Each *Agrobacterium* strain was inoculated to an LB medium (containing 100 mg/L ampicillin, 50 mg/L gentamicin, and 100 mg/L kanamycin) and shake-cultured at 28° C. for 22 hours until the turbidity reached O.D. 600=0.8. The obtained bacterial solution was centrifuged to collect bacterial cells, which were then suspended in an MS liquid medium. A bacterial solution was prepared at the bacterial cell density of O.D. 600=0.5. The tomato explants were dipped in the prepared bacterial solution for 20 minutes and then cocultivated at 28° C. for 72 hours under dark conditions. The cocultivation medium used was prepared by the addition of 3% glucose, 200 µM acetosyringone, and 1.5 mg/L zeatin to an MS medium.

After the completion of the cocultivation, the tomato cotyledon explants were subjected to GUS staining to evaluate the gene transfer efficiency. Specifically, the cocultivated tomato cotyledon explants were dipped in a 100 mM phosphate buffer solution containing EDTA (10 mM), potassium ferricyanide (5 mM), potassium ferrocyanide (5 mM), Triton X-100 (0.1%), and 5-bromo-4-chloro-3-indoxyl-glucuronide (X-Glu) (0.5 mg/L) and incubated overnight at 37° C. By this treatment, the substrate X-Glu is degraded by the function of the GUS gene product in GUS gene-introduced cells so that the cells are stained dark blue. After the overnight incubation at 37° C., in order to observe the degree of staining, the tomato explants were transferred from the phosphate buffer solution to 70% ethanol to terminate the GUS staining reaction while decolorizing chlorophyll. The 70% ethanol was replaced with a fresh one twice, and the tomato explants were finally dipped in 100% ethanol. After the complete decolorization of chlorophyll, the frequency of appearance of explants stained dark blue was examined. In this examination, the staining levels were divided to 0 to 5 (FIG. 7B), and the frequency of appearance of explants at each staining level was evaluated. 0 means that no GUS stain spot was observed, and numerals closer to 5 from 1 mean that GUS-stained regions occupy a larger proportion of the explants. Similar results were obtained in 3 experiments. 30 tomato cotyledon sections were used per one experiment. The results are shown in FIG. 7.

When the GUS gene transfer to the tomato was compared between the *Agrobacterium* strain GV2260(pBBRgabT, pIG121-Hm) provided with the gabT activity and the control *Agrobacterium* strain GV2260(pBBR1MCS-5, pIG121-Hm), the proportion (%) of the number of explants in which GUS spots were observed, and the average frequency of appearance of GUS spots per explant were significantly increased in the *Agrobacterium* strain provided with the gabT activity (FIG. 7A). This demonstrated that the *Agrobacterium* strain having excellent gene transfer ability to plants can be prepared by imparting the GABA transaminase activity to the *Agrobacterium*.

[Example 7] Evaluation of Gene Transfer Efficiency to Plant-2

Next, the *Agrobacterium* strain GV2260(pBBRgabT, pEKH$_2$) provided with the GABA transaminase activity, the *Agrobacterium* strain GV2260(pBBRacdS/gabT, pEKH$_2$) provided with the GABA transaminase activity and the ACC deaminase activity, the *Agrobacterium* strain GV2260(pBBRacdS, pEKH$_2$) provided with the ACC deaminase activity, and the control *Agrobacterium* strain GV2260 (pBBR1MCS-5, pEKH$_2$) were each used to evaluate their transfer efficiency of the GUS gene to a monocotyledon *erianthus* (*Erianthus ravennae*). Ripe *erianthus* seeds were cultured in an MS medium containing 3% maltose, 2 mg/L 2,4-dichlorophenoxyacetic acid, 0.2% bacterial alkaline phosphatase (BAP), and 0.3% Gelrite to induce calli. The *erianthus* calli were planted on a fresh medium 3 days before *Agrobacterium* infection. Each *Agrobacterium* strain was cultured in 2 mL of an LB medium containing 50 mg/L gentamicin, 50 mg/L spectinomycin, and 100 mg/L ampicillin until reaching a steady state (preculture). Then, the precultures were diluted 1000-fold, and main culture was started. After 22 hours into the main culture, bacterial cells were collected at the time when the turbidity reached O.D. 600=0.8. The collected *Agrobacterium* cells were resuspended in a liquid MS medium to adjust the turbidity to O.D. 600=0.4 to 0.5. The *erianthus* calli were placed in the *Agrobacterium* suspension and left under 0.8 MPa for 10 minutes, and this treatment was repeated twice. Subsequently, the *erianthus* calli dipped in the *Agrobacterium* suspension were recovered and cocultivated at 28° C. for 72 hours under dark conditions. The cocultivation medium used was prepared by the addition of 3% glucose and 200 µM acetosyringone to an MS medium.

Figure 8:
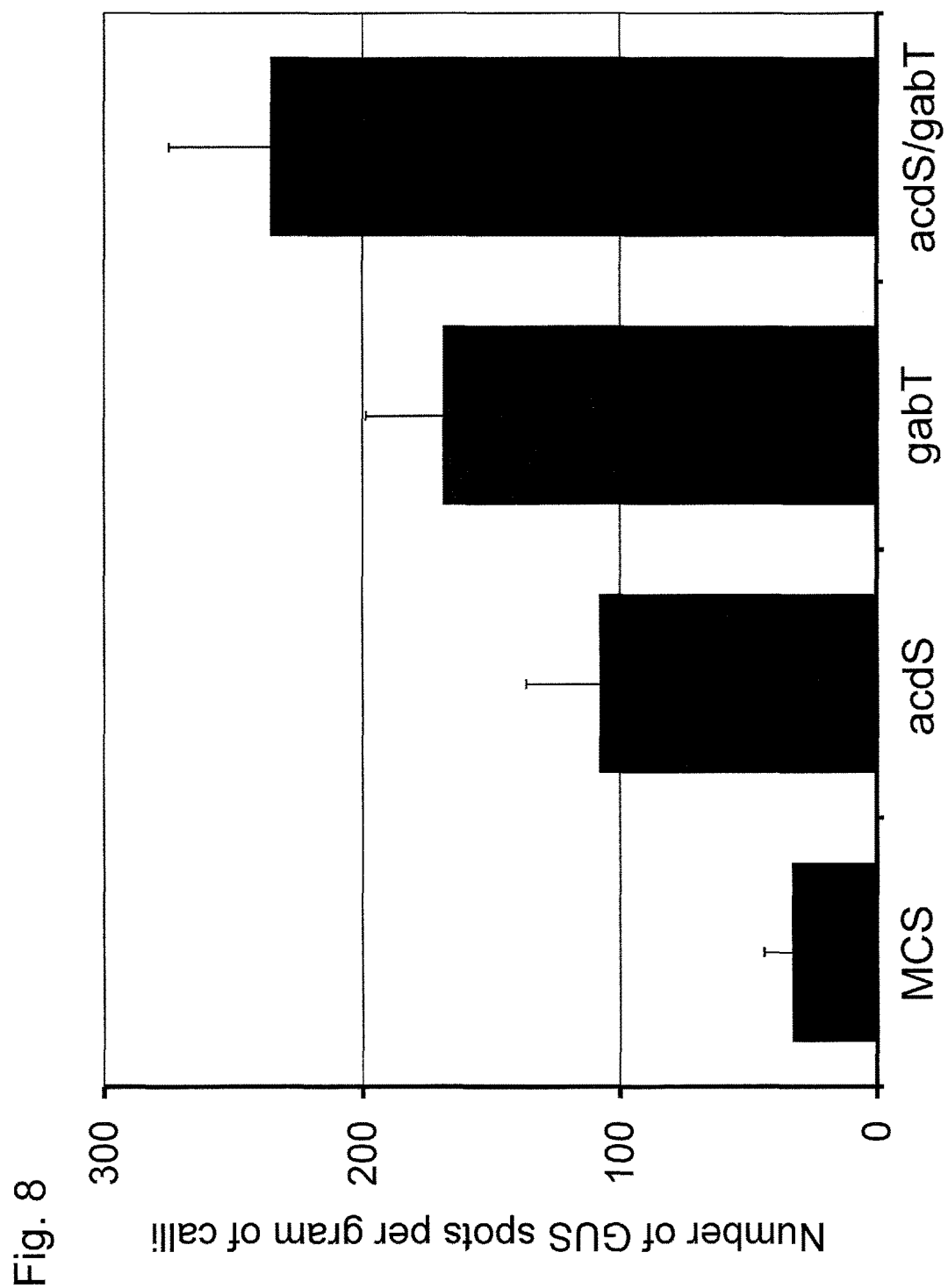
FIG. 8 shows the gene transfer efficiency of *Agrobacterium* to erianthus. MCS: *Agrobacterium* strain GV2260 (pBBR1MCS-5, pEKH$_2$); acdS: *Agrobacterium* strain GV2260 (pBBRacdS, pEKH$_2$); gabT: *Agrobacterium* strain GV2260 (pBBRgabT, pEKH$_2$); and acdS/gabT: *Agrobacterium* strain GV2260 (pBBRacdS/gabT, pEKH$_2$). n=3. The error bar indicates standard deviation. In one experiment, 1 to 2 g of calli was used.

After the completion of the cocultivation, the *erianthus* calli were subjected to GUS staining to evaluate the gene transfer efficiency. Specifically, the cocultivated *erianthus* calli were dipped in a 100 mM phosphate buffer solution containing EDTA (10 mM), potassium ferricyanide (5 mM), potassium ferrocyanide (5 mM), Triton X-100 (0.1%), and 5-bromo-4-chloro-3-indoxyl-glucuronide (X-Glu) (0.5 mg/L) and incubated overnight at 37° C. By this treatment, the substrate X-Glu is degraded by the function of the GUS gene product in GUS gene-introduced cells so that the cells are stained dark blue. After the overnight incubation at 37° C., the *erianthus* calli were transferred to 70% ethanol to terminate the degradation reaction of the substrate X-Glu. The 70% ethanol was replaced with a fresh one twice, and the *erianthus* calli were finally dipped in 100% ethanol. The number of GUS spots stained dark blue in the calli was counted. On the basis of the results, the gene transfer ability of each bacterial strain was evaluated. The results are shown in FIG. 8.

When the GUS gene transfer to the *erianthus* was compared between the *Agrobacterium* strain GV2260(pBBRgabT, pEKH$_2$) provided with the GABA transaminase activity and the control *Agrobacterium* strain GV2260 (pBBR1MCS-5, pEKH$_2$), the number of GUS spots per g of the calli was significantly increased in the *Agrobacterium* strain provided with the GABA transaminase activity. This demonstrated that the bacterial strain capable of gene transfer to various plants with high frequency can be prepared by imparting the GABA transaminase activity to the *Agrobacterium*. Even as compared with the *Agrobacterium* provided with the ACC deaminase activity alone, the *Agrobacterium* provided with the GABA transaminase activity had evidently higher gene transfer efficiency. The *Agrobacterium* strain GV2260(pBBRacdS/gabT, pEKH$_2$) provided with both of the ACC deaminase activity and the GABA transaminase activity had a further increased number of GUS spots appearing per g of the *erianthus* calli and particularly higher gene transfer ability, as compared with the *Agrobacterium* strain provided with the ACC deaminase activity alone and the *Agrobacterium* strain provided with the GABA transaminase alone. These results indicate that the gene transfer ability of the *Agrobacterium* can be enhanced more effectively by imparting the GABA transaminase activity to the *Agrobacterium* than by imparting thereto the ACC deaminase activity alone. These results demonstrated that the imparting of the GABA transaminase activity can improve the gene transfer efficiency very significantly, particularly, to a plant such as *erianthus*, for which the inhibition of ethylene production by the ACC deaminase activity imparted to the *Agrobacterium* may not much improve the gene transfer efficiency. These results also demonstrated that the imparting of both of the ACC deaminase activity and the GABA transaminase activity can further enhance the gene transfer efficiency.

[Example 8] Evaluation of Gene Transfer Efficiency to Plant-3

The *Agrobacterium* strain GV2260(pBBRgabT, pIG121-Hm) and the *Agrobacterium* strain GV2260(pBBRacdS/gabT, pIG121-Hm) harboring the introduced GABA transaminase gene were used to evaluate their gene transfer efficiency to a dicotyledon tomato. In this context, the genes to be transferred to the plant were a GUS gene, a kanamycin resistance gene, and a hygromycin resistance gene that are contained in the T-DNA region of the binary vector pIG121-Hm (Hiei et al., Plant J., 6 (2): 271-282 (1994)). Since selection using hygromycin is impossible for tomato, the kanamycin resistance gene was used as a marker for gene transfer in this Example.

First, the *Agrobacterium* strain GV2260(pBBRgabT, pIG121-Hm), the *Agrobacterium* strain GV2260(pBBRacdS/gabT, pIG121-Hm), and the control *Agrobacterium* strain GV2260(pBBR1MCS-5, pIG121-Hm) and *Agrobacterium* strain GV2260(pBBRacdS, pIG121-Hm) were each used to transform a dicotyledon tomato (*Solanum lycopersicum* 'Micro Tom') and evaluated for the preparation efficiency of stable transformants. Specifically, tomato seeds were aseptically inoculated on ½ MS (Murashige-Skoog) medium containing 1.5% sucrose and allowed to grow. The upper and lower regions of the obtained cotyledons were cut off, and evenly divided sections were used as tomato explants in gene transfer (sample sections). Each *Agrobacterium* strain was inoculated to an LB medium (containing 100 mg/L ampicillin, 50 mg/L gentamicin, and 100 mg/L kanamycin) and shake-cultured at 28° C. for 22 hours until the turbidity reached O.D. 600=0.8. The obtained bacterial solution was centrifuged to collect bacterial cells, which were then suspended in an MS liquid medium. A bacterial solution was prepared at the bacterial cell density of O.D. 600=0.5. The tomato explants were dipped in the prepared bacterial solution for 20 minutes and then cocultivated at 28° C. for 72 hours under dark conditions. The cocultivation medium used was prepared by the addition of 3% glucose, 200 μM acetosyringone, 1.5 mg/L zeatin, and 0.3% gellangum to an MS medium followed by pH adjustment to 5.2.

After the completion of the cocultivation, the tomato explants were planted to a bacterial elimination and callus induction medium. The bacterial elimination and callus induction medium used was prepared by the addition of 3% sucrose, 1.5 mg/L zeatin, 0.3% gellangum, 100 mg/L kanamycin, and 375 mg/L Augmentin to an MS medium followed by pH adjustment to 5.8. The tomato explants were cultivated in this bacterial elimination and callus induction medium at 25° C. for 3 to 4 weeks under conditions of 16-hour day length and 60 μmol$^{-2}$S$^{-1}$ light, and shoots were then formed. The calli with the formed shoots were transplanted to a shoot elongation medium. The shoot elongation medium used was prepared by the addition of 3% sucrose, 1.0 mg/L zeatin, 0.3% gellangum, 100 mg/L kanamycin, and 375 mg/L Augmentin to an MS medium followed by pH adjustment to 5.8. After elongation of the shoots to 1 to 2 cm, the shoots were cut off and transplanted to a rooting medium. The rooting medium used was prepared by the addition of 15% sucrose, 0.3% gellangum, 100 mg/L kanamycin, and 375 mg/L Augmentin to ½ MS medium followed by pH adjustment to 5.8. Individuals rooted within 2 weeks in the rooting medium (rooted individuals) were selected as candidates of transformants. Individuals having lateral roots branching off from the taproot were determined as the rooted individuals. Diploids were selected from the rooted individuals using a flow cytometer. The genome was extracted from each of the diploid individuals and subjected to Southern hybridization with each transgene fragment as a probe to confirm gene transfer to the genome. Several experiments were conducted, and the average ratio (transformation efficiency) of the number of the obtained gene-transferred individuals (Southern hybridization-positive) to the number of sample sections (80 to 156 sections were used per bacterial strain in each experiment) was calculated (Table 1).

TABLE 1

| | Transformation efficiency (average %) |
|---|---|
| MCS | 4.3% |
| acdS | 9.6% |

TABLE 1-continued

| | Transformation efficiency (average %) |
|---|---|
| gabT | 10.1% |
| acdS/gabT | 13.5% |

MCS: GV2260(pBBR1MCS-5, pIG121-Hm)
acdS: GV2260(pBBRacdS, pIG121-Hm)
gabT: GV2260(pBBRgabT, pIG121-Hm)
acdS/gabT: GV2260(pBBRacdS/gabT, pIG121-Hm)

The *Agrobacterium* strain GV2260(pBBRgabT, pIG121-Hm) provided with the gabT activity exhibited transformation efficiency (gene transfer efficiency to the genome of individual) significantly elevated by approximately 235%, as compared with the *Agrobacterium* strain GV2260 (pBBR1MCS-5, pIG121-Hm) used as a control. The *Agrobacterium* strain GV2260(pBBRacdS/gabT, pIG121-Hm) harboring both of the introduced genes acdS and gabT exhibited further elevated transformation efficiency, as compared with the control *Agrobacterium* strain GV2260 (pBBR1MCS-5, pIG121-Hm) and the *Agrobacterium* strains GV2260(pBBRacdS, pIG121-Hm) and GV2260(pBBRgabT, pIG121-Hm) harboring either acdS or gabT introduced. These results further supported that the gene transfer ability of the *Agrobacterium* strain can be further enhanced by imparting the GABA transaminase activity together with the acdS activity to the *Agrobacterium*.

INDUSTRIAL APPLICABILITY

The present invention can be used for improving the gene transfer efficiency of plant transformation based on the *Agrobacterium* method. The *Agrobacterium* of the present invention and the method of the present invention can be used, for example, in order to improve the production efficiency of recombinant plants for plant species on which *Agrobacterium*-mediated gene transfer has previously been reported, and in order to produce recombinant plants for plant species for which gene transfer has heretofore been considered to be difficult. The present invention enables breeding using gene recombination for a wide range of plant species.

All publications, patents, and patent applications are incorporated herein by reference in their entirety.

Free Text of Sequence Listing
    SEQ ID NO: 1: Nucleotide sequence encoding an *Escherichia coli* strain-derived GABA transaminase protein
    SEQ ID NO: 2: GABA transaminase protein
    SEQ ID NO: 3: Primer gabTF
    SEQ ID NO: 4: Primer gabTR
    SEQ ID NO: 5: Nucleotide sequence encoding a GABA transaminase protein with β galactosidase-derived 33 amino acids added thereto
    SEQ ID NO: 6: GABA transaminase protein with β galactosidase-derived 33 amino acids added thereto
    SEQ ID NO: 7: Primer acdS-for
    SEQ ID NO: 8: Primer gabT-Rev
    SEQ ID NO: 9: gabT fragment 2
    SEQ ID NO: 10: Primer amp_ter-for2
    SEQ ID NO: 11: Primer amp_ter-rev2
    SEQ ID NO: 12: amp-term fragment
    SEQ ID NO: 13: ACC deaminase gene
    SEQ ID NO: 14: ACC deaminase protein
    SEQ ID NO: 15: Primer GUSF
    SEQ ID NO: 16: Primer GUSR

What is claimed is:

1. A transformed *Agrobacterium* which harbors a foreign γ-aminobutyric acid (GABA) transaminase gene and exhibits improved gene transfer efficiency, wherein the foreign GABA transaminase gene is not present in a T-DNA region.

2. The transformed *Agrobacterium* according to claim 1, which further harbors a foreign 1-aminocyclopropane-1-carboxylate (ACC) deaminase gene, wherein the foreign ACC deaminase gene is not present in a T-DNA region.

3. The transformed *Agrobacterium* according to claim 1, wherein the transformed *Agrobacterium* harbors the foreign GABA transaminase gene in a vector.

4. The transformed *Agrobacterium* according to claim 1, which further comprises a binary vector comprising a T-DNA region.

5. The transformed *Agrobacterium* according to claim 1, wherein the GABA transaminase gene is derived from a bacterium.

6. The transformed *Agrobacterium* according to claim 2, wherein the ACC deaminase gene is derived from a bacterium.

7. A method for producing a transformed plant, comprising carrying out gene transfer to a plant using the transformed *Agrobacterium* according to claim 1.

8. The method according to claim 7, wherein the plant is a monocotyledon or a dicotyledon.

9. The method according to claim 8, wherein the monocotyledon is a plant of the family Poaceae.

10. The method according to claim 8, wherein the dicotyledon is a plant of the family Solanaceae.

11. The transformed *Agrobacterium* according to claim 2, which further comprises a binary vector comprising a T-DNA region.

12. A method for producing a transformed plant, comprising carrying out gene transfer to a plant using the transformed *Agrobacterium* according to claim 2.

13. The method according to claim 12, wherein the plant is a monocotyledon or a dicotyledon.

14. The method according to claim 13, wherein the monocotyledon is a plant of the family Poaceae.

15. The method according to claim 13, wherein the dicotyledon is a plant of the family Solanaceae.

16. The transformed *Agrobacterium* according to claim 2, wherein the transformed *Agrobacterium* harbors the GABA transaminase gene and the ACC deaminase gene in a vector.

* * * * *

SEQUENCE LISTING

<160> NUMBER OF SEQ ID NOS: 16

<210> SEQ ID NO 1
<211> LENGTH: 1281
<212> TYPE: DNA
<213> ORGANISM: Escherichia coli
<220> FEATURE:
<223> OTHER INFORMATION: nucleotide sequence encoding Escherichia coli-
      derived GABA aminotransferase protein
<220> FEATURE:
<221> NAME/KEY: CDS
<222> LOCATION: (1)..(1281)

<400> SEQUENCE: 1

```
atg aac agc aat aaa gag tta atg cag cgc cgc agt cag gcg att ccc      48
Met Asn Ser Asn Lys Glu Leu Met Gln Arg Arg Ser Gln Ala Ile Pro
1               5                   10                  15 cgt ggc gtt ggg caa att cac ccg att ttc gct gac cgc gcg gaa aac      96
Arg Gly Val Gly Gln Ile His Pro Ile Phe Ala Asp Arg Ala Glu Asn
            20                  25                  30 tgc cgg gtg tgg gac gtt gaa ggc cgt gag tat ctt gat ttc gcg ggc     144
Cys Arg Val Trp Asp Val Glu Gly Arg Glu Tyr Leu Asp Phe Ala Gly
        35                  40                  45 ggg att gcg gtg ctc aat acc ggg cac ctg cat ccg aag gtg gtg gcc     192
Gly Ile Ala Val Leu Asn Thr Gly His Leu His Pro Lys Val Val Ala
    50                  55                  60 gcg gtg gaa gcg cag ttg aaa aaa ctg tcg cac acc tgc ttc cag gtg     240
Ala Val Glu Ala Gln Leu Lys Lys Leu Ser His Thr Cys Phe Gln Val
65                  70                  75                  80 ctg gct tac gag ccg tat ctg gag ctg tgc gag att atg aat cag aag     288
Leu Ala Tyr Glu Pro Tyr Leu Glu Leu Cys Glu Ile Met Asn Gln Lys
                85                  90                  95 gtg ccg ggc gat ttc gcc aag aaa acg ctg ctg gtt acg acc ggt tcc     336
Val Pro Gly Asp Phe Ala Lys Lys Thr Leu Leu Val Thr Thr Gly Ser
            100                 105                 110 gaa gcg gtg gaa aac gcg gta aaa atc gcc cgc gcc gcc acc aaa cgt     384
Glu Ala Val Glu Asn Ala Val Lys Ile Ala Arg Ala Ala Thr Lys Arg
        115                 120                 125 agc ggc acc atc gct ttt agc ggc gcg tat cac ggg cgc acg cat tac     432
Ser Gly Thr Ile Ala Phe Ser Gly Ala Tyr His Gly Arg Thr His Tyr
    130                 135                 140 acg ctg gcg ctg acc ggc aag gtg aat ccg tac tct gcg ggc atg ggg     480
Thr Leu Ala Leu Thr Gly Lys Val Asn Pro Tyr Ser Ala Gly Met Gly
145                 150                 155                 160 ctg atg ccg ggt cat gtt tat cgc gcg ctt tat cct tgc ccg ctg cac     528
Leu Met Pro Gly His Val Tyr Arg Ala Leu Tyr Pro Cys Pro Leu His
                165                 170                 175 ggc ata agc gag gat gac gct atc gcc agc atc cac cgg atc ttc aaa     576
Gly Ile Ser Glu Asp Asp Ala Ile Ala Ser Ile His Arg Ile Phe Lys
            180                 185                 190 aat gat gcc gcg ccg gaa gat atc gcc gcc atc gtg att gag ccg gtt     624
Asn Asp Ala Ala Pro Glu Asp Ile Ala Ala Ile Val Ile Glu Pro Val
        195                 200                 205 cag ggc gaa ggc ggt ttc tac gcc tcg tcg cca gcc ttt atg cag cgt     672
Gln Gly Glu Gly Gly Phe Tyr Ala Ser Ser Pro Ala Phe Met Gln Arg
    210                 215                 220 tta cgc gct ctg tgt gac gag cac ggg atc atg ctg att gcc gat gaa     720
Leu Arg Ala Leu Cys Asp Glu His Gly Ile Met Leu Ile Ala Asp Glu
225                 230                 235                 240 gtg cag agc ggc gcg ggg cgt acc ggc acg ctg ttt gcg atg gag cag     768
Val Gln Ser Gly Ala Gly Arg Thr Gly Thr Leu Phe Ala Met Glu Gln
                245                 250                 255
```

-continued

```
atg ggc gtt gcg ccg gat ctt acc acc ttt gcg aaa tcg atc gcg ggc    816
Met Gly Val Ala Pro Asp Leu Thr Thr Phe Ala Lys Ser Ile Ala Gly
    260                 265                 270 ggc ttc ccg ctg gcg ggc gtc acc ggg cgc gcg gaa gta atg gat gcc    864
Gly Phe Pro Leu Ala Gly Val Thr Gly Arg Ala Glu Val Met Asp Ala
275                 280                 285 gtc gct cca ggc ggt ctg ggc ggc acc tat gcg ggt aac ccg att gcc    912
Val Ala Pro Gly Gly Leu Gly Gly Thr Tyr Ala Gly Asn Pro Ile Ala
    290                 295                 300 tgc gtg gct gcg ctg gaa gtg ttg aag gtg ttt gag cag gaa aat ctg    960
Cys Val Ala Ala Leu Glu Val Leu Lys Val Phe Glu Gln Glu Asn Leu
305                 310                 315                 320 ctg caa aaa gcc aac gat ctg ggg cag aag ttg aaa gac gga ttg ctg    1008
Leu Gln Lys Ala Asn Asp Leu Gly Gln Lys Leu Lys Asp Gly Leu Leu
                325                 330                 335 gcg ata gcc gaa aaa cac ccg gag atc ggc gac gta cgc ggg ctg ggg    1056
Ala Ile Ala Glu Lys His Pro Glu Ile Gly Asp Val Arg Gly Leu Gly
            340                 345                 350 gcg atg atc gcc att gag ctg ttt gaa gac ggc gat cac aac aag ccg    1104
Ala Met Ile Ala Ile Glu Leu Phe Glu Asp Gly Asp His Asn Lys Pro
        355                 360                 365 gac gcc aaa ctc acc gcc gag atc gtg gct cgc gcc cgc gat aaa ggc    1152
Asp Ala Lys Leu Thr Ala Glu Ile Val Ala Arg Ala Arg Asp Lys Gly
    370                 375                 380 ctg att ctt ctc tcc tgc ggc ccg tat tac aac gtg ctg cgc atc ctt    1200
Leu Ile Leu Leu Ser Cys Gly Pro Tyr Tyr Asn Val Leu Arg Ile Leu
385                 390                 395                 400 gta ccg ctc acc att gaa gac gct cag atc cgt cag ggt ctg gag atc    1248
Val Pro Leu Thr Ile Glu Asp Ala Gln Ile Arg Gln Gly Leu Glu Ile
                405                 410                 415 atc agc cag tgt ttt gat gag gcg aag cag tag                        1281
Ile Ser Gln Cys Phe Asp Glu Ala Lys Gln
            420                 425

<210> SEQ ID NO 2
<211> LENGTH: 426
<212> TYPE: PRT
<213> ORGANISM: Escherichia coli
<220> FEATURE:
<223> OTHER INFORMATION: GABA aminotransferase protein

<400> SEQUENCE: 2

Met Asn Ser Asn Lys Glu Leu Met Gln Arg Ser Gln Ala Ile Pro
1               5                   10                  15

Arg Gly Val Gly Gln Ile His Pro Ile Phe Ala Asp Arg Ala Glu Asn
            20                  25                  30

Cys Arg Val Trp Asp Val Glu Gly Arg Glu Tyr Leu Asp Phe Ala Gly
        35                  40                  45

Gly Ile Ala Val Leu Asn Thr Gly His Leu His Pro Lys Val Val Ala
    50                  55                  60

Ala Val Glu Ala Gln Leu Lys Lys Leu Ser His Thr Cys Phe Gln Val
65                  70                  75                  80

Leu Ala Tyr Glu Pro Tyr Leu Glu Leu Cys Glu Ile Met Asn Gln Lys
                85                  90                  95

Val Pro Gly Asp Phe Ala Lys Lys Thr Leu Leu Val Thr Thr Gly Ser
            100                 105                 110

Glu Ala Val Glu Asn Ala Val Lys Ile Ala Arg Ala Ala Thr Lys Arg
        115                 120                 125
```

Ser Gly Thr Ile Ala Phe Ser Gly Ala Tyr His Gly Arg Thr His Tyr
    130                 135                 140

Thr Leu Ala Leu Thr Gly Lys Val Asn Pro Tyr Ser Ala Gly Met Gly
145                 150                 155                 160

Leu Met Pro Gly His Val Tyr Arg Ala Leu Tyr Pro Cys Pro Leu His
                165                 170                 175

Gly Ile Ser Glu Asp Asp Ala Ile Ala Ser Ile His Arg Ile Phe Lys
            180                 185                 190

Asn Asp Ala Ala Pro Glu Asp Ile Ala Ile Val Ile Glu Pro Val
        195                 200                 205

Gln Gly Glu Gly Phe Tyr Ala Ser Ser Pro Ala Phe Met Gln Arg
210                 215                 220

Leu Arg Ala Leu Cys Asp Glu His Gly Ile Met Leu Ile Ala Asp Glu
225                 230                 235                 240

Val Gln Ser Gly Ala Gly Arg Thr Gly Thr Leu Phe Ala Met Glu Gln
                245                 250                 255

Met Gly Val Ala Pro Asp Leu Thr Thr Phe Ala Lys Ser Ile Ala Gly
            260                 265                 270

Gly Phe Pro Leu Ala Gly Val Thr Gly Arg Ala Glu Val Met Asp Ala
        275                 280                 285

Val Ala Pro Gly Gly Leu Gly Gly Thr Tyr Ala Gly Asn Pro Ile Ala
290                 295                 300

Cys Val Ala Ala Leu Glu Val Leu Lys Val Phe Glu Gln Glu Asn Leu
305                 310                 315                 320

Leu Gln Lys Ala Asn Asp Leu Gly Gln Lys Leu Lys Asp Gly Leu Leu
                325                 330                 335

Ala Ile Ala Glu Lys His Pro Glu Ile Gly Asp Val Arg Gly Leu Gly
            340                 345                 350

Ala Met Ile Ala Ile Glu Leu Phe Glu Asp Gly Asp His Asn Lys Pro
        355                 360                 365

Asp Ala Lys Leu Thr Ala Glu Ile Val Ala Arg Ala Arg Asp Lys Gly
370                 375                 380

Leu Ile Leu Leu Ser Cys Gly Pro Tyr Tyr Asn Val Leu Arg Ile Leu
385                 390                 395                 400

Val Pro Leu Thr Ile Glu Asp Ala Gln Ile Arg Gln Gly Leu Glu Ile
                405                 410                 415

Ile Ser Gln Cys Phe Asp Glu Ala Lys Gln
            420                 425

<210> SEQ ID NO 3
<211> LENGTH: 27
<212> TYPE: DNA
<213> ORGANISM: Artificial
<220> FEATURE:
<223> OTHER INFORMATION: primer gabTF

<400> SEQUENCE: 3
aagcttaatg aacagcaata aagagtt                                27

<210> SEQ ID NO 4
<211> LENGTH: 29
<212> TYPE: DNA
<213> ORGANISM: Artificial
<220> FEATURE:
<223> OTHER INFORMATION: primer gabTR

<400> SEQUENCE: 4

-continued

```
tctagactac tgcttcgcct catcaaaac                                      29
```

<210> SEQ ID NO 5
<211> LENGTH: 1380
<212> TYPE: DNA
<213> ORGANISM: Artificial
<220> FEATURE:
<223> OTHER INFORMATION: nucleotide sequence encoding GABA
      aminotransferase protein with added lacZ-derived 33 amino acids
<220> FEATURE:
<221> NAME/KEY: CDS
<222> LOCATION: (1)..(1380)

<400> SEQUENCE: 5

```
atg acc atg att acg cca agc gcg caa tta acc ctc act aaa ggg aac    48
Met Thr Met Ile Thr Pro Ser Ala Gln Leu Thr Leu Thr Lys Gly Asn
1               5                   10                  15 aaa agc tgg gta ccg ggc ccc ccc tcg agg tcg acg gta tcg ata agc    96
Lys Ser Trp Val Pro Gly Pro Pro Ser Arg Ser Thr Val Ser Ile Ser
            20                  25                  30 tta atg aac agc aat aaa gag tta atg cag cgc cgc agt cag gcg att   144
Leu Met Asn Ser Asn Lys Glu Leu Met Gln Arg Arg Ser Gln Ala Ile
        35                  40                  45 ccc cgt ggc gtt ggg caa att cac ccg att ttc gct gac cgc gcg gaa   192
Pro Arg Gly Val Gly Gln Ile His Pro Ile Phe Ala Asp Arg Ala Glu
50                  55                  60 aac tgc cgg gtg tgg gac gtt gaa ggc cgt gag tat ctt gat ttc gcg   240
Asn Cys Arg Val Trp Asp Val Glu Gly Arg Glu Tyr Leu Asp Phe Ala
65                  70                  75                  80 ggc ggg att gcg gtg ctc aat acc ggg cac ctg cat ccg aag gtg gtg   288
Gly Gly Ile Ala Val Leu Asn Thr Gly His Leu His Pro Lys Val Val
                85                  90                  95 gcc gcg gtg gaa gcg cag ttg aaa aaa ctg tcg cac acc tgc ttc cag   336
Ala Ala Val Glu Ala Gln Leu Lys Lys Leu Ser His Thr Cys Phe Gln
            100                 105                 110 gtg ctg gct tac gag ccg tat ctg gag ctg tgc gag att atg aat cag   384
Val Leu Ala Tyr Glu Pro Tyr Leu Glu Leu Cys Glu Ile Met Asn Gln
        115                 120                 125 aag gtg ccg ggc gat ttc gcc aag aaa acg ctg ctg gtt acg acc ggt   432
Lys Val Pro Gly Asp Phe Ala Lys Lys Thr Leu Leu Val Thr Thr Gly
130                 135                 140 tcc gaa gcg gtg gaa aac gcg gta aaa atc gcc cgc gcc gcc acc aaa   480
Ser Glu Ala Val Glu Asn Ala Val Lys Ile Ala Arg Ala Ala Thr Lys
145                 150                 155                 160 cgt agc ggc acc atc gct ttt agc ggc gcg tat cac ggg cgc acg cat   528
Arg Ser Gly Thr Ile Ala Phe Ser Gly Ala Tyr His Gly Arg Thr His
                165                 170                 175 tac acg ctg gcg ctg acc ggc aag gtg aat ccg tac tct gcg ggc atg   576
Tyr Thr Leu Ala Leu Thr Gly Lys Val Asn Pro Tyr Ser Ala Gly Met
            180                 185                 190 ggg ctg atg ccg ggt cat gtt tat cgc gcg ctt tat cct tgc ccg ctg   624
Gly Leu Met Pro Gly His Val Tyr Arg Ala Leu Tyr Pro Cys Pro Leu
        195                 200                 205 cac ggc ata agc gag gat gac gct atc gcc agc atc cac cgg atc ttc   672
His Gly Ile Ser Glu Asp Asp Ala Ile Ala Ser Ile His Arg Ile Phe
210                 215                 220 aaa aat gat gcc gcg ccg gaa gat atc gcc gcc atc gtg att gag ccg   720
Lys Asn Asp Ala Ala Pro Glu Asp Ile Ala Ala Ile Val Ile Glu Pro
225                 230                 235                 240 gtt cag ggc gaa ggc ggt ttc tac gcc tcg tcg cca gcc ttt atg cag   768
Val Gln Gly Glu Gly Gly Phe Tyr Ala Ser Ser Pro Ala Phe Met Gln
                245                 250                 255
```

-continued

```
cgt tta cgc gct ctg tgt gac gag cac ggg atc atg ctg att gcc gat    816
Arg Leu Arg Ala Leu Cys Asp Glu His Gly Ile Met Leu Ile Ala Asp
        260                 265                 270 gaa gtg cag agc ggc gcg ggg cgt acc ggc acg ctg ttt gcg atg gag    864
Glu Val Gln Ser Gly Ala Gly Arg Thr Gly Thr Leu Phe Ala Met Glu
            275                 280                 285 cag atg ggc gtt gcg ccg gat ctt acc acc ttt gcg aaa tcg atc gcg    912
Gln Met Gly Val Ala Pro Asp Leu Thr Thr Phe Ala Lys Ser Ile Ala
    290                 295                 300 ggc ggc ttc ccg ctg gcg ggc gtc acc ggg cgc gcg gaa gta atg gat    960
Gly Gly Phe Pro Leu Ala Gly Val Thr Gly Arg Ala Glu Val Met Asp
305                 310                 315                 320 gcc gtc gct cca ggc ggt ctg ggc ggc acc tat gcg ggt aac ccg att   1008
Ala Val Ala Pro Gly Gly Leu Gly Gly Thr Tyr Ala Gly Asn Pro Ile
                325                 330                 335 gcc tgc gtg gct gcg ctg gaa gtg ttg aag gtg ttt gag cag gaa aat   1056
Ala Cys Val Ala Ala Leu Glu Val Leu Lys Val Phe Glu Gln Glu Asn
            340                 345                 350 ctg ctg caa aaa gcc aac gat ctg ggg cag aag ttg aaa gac gga ttg   1104
Leu Leu Gln Lys Ala Asn Asp Leu Gly Gln Lys Leu Lys Asp Gly Leu
    355                 360                 365 ctg gcg ata gcc gaa aaa cac ccg gag atc ggc gac gta cgc ggg ctg   1152
Leu Ala Ile Ala Glu Lys His Pro Glu Ile Gly Asp Val Arg Gly Leu
370                 375                 380 ggg gcg atg atc gcc att gag ctg ttt gaa gac ggc gat cac aac aag   1200
Gly Ala Met Ile Ala Ile Glu Leu Phe Glu Asp Gly Asp His Asn Lys
385                 390                 395                 400 ccg gac gcc aaa ctc acc gcc gag atc gtg gct cgc gcc cgc gat aaa   1248
Pro Asp Ala Lys Leu Thr Ala Glu Ile Val Ala Arg Ala Arg Asp Lys
                405                 410                 415 ggc ctg att ctt ctc tcc tgc ggc ccg tat tac aac gtg ctg cgc atc   1296
Gly Leu Ile Leu Leu Ser Cys Gly Pro Tyr Tyr Asn Val Leu Arg Ile
            420                 425                 430 ctt gta ccg ctc acc att gaa gac gct cag atc cgt cag ggt ctg gag   1344
Leu Val Pro Leu Thr Ile Glu Asp Ala Gln Ile Arg Gln Gly Leu Glu
    435                 440                 445 atc atc agc cag tgt ttt gat gag gcg aag cag tag              1380
Ile Ile Ser Gln Cys Phe Asp Glu Ala Lys Gln
    450                 455

<210> SEQ ID NO 6
<211> LENGTH: 459
<212> TYPE: PRT
<213> ORGANISM: Artificial
<220> FEATURE:
<223> OTHER INFORMATION: GABA aminotransferase protein with added
      lacZ-derived 33 amino acids

<400> SEQUENCE: 6

Met Thr Met Ile Thr Pro Ser Ala Gln Leu Thr Leu Thr Lys Gly Asn
1               5                   10                  15

Lys Ser Trp Val Pro Gly Pro Pro Ser Arg Ser Thr Val Ser Ile Ser
            20                  25                  30

Leu Met Asn Ser Asn Lys Glu Leu Met Gln Arg Arg Ser Gln Ala Ile
        35                  40                  45

Pro Arg Gly Val Gly Gln Ile His Pro Ile Phe Ala Asp Arg Ala Glu
    50                  55                  60

Asn Cys Arg Val Trp Asp Val Glu Gly Arg Glu Tyr Leu Asp Phe Ala
65                  70                  75                  80
```

```
Gly Gly Ile Ala Val Leu Asn Thr Gly His Leu His Pro Lys Val Val
                    85                  90                  95

Ala Ala Val Glu Ala Gln Leu Lys Lys Leu Ser His Thr Cys Phe Gln
            100                 105                 110

Val Leu Ala Tyr Glu Pro Tyr Leu Glu Leu Cys Glu Ile Met Asn Gln
            115                 120                 125

Lys Val Pro Gly Asp Phe Ala Lys Lys Thr Leu Leu Val Thr Thr Gly
            130                 135                 140

Ser Glu Ala Val Glu Asn Ala Val Lys Ile Ala Arg Ala Ala Thr Lys
145                 150                 155                 160

Arg Ser Gly Thr Ile Ala Phe Ser Gly Ala Tyr His Gly Arg Thr His
                165                 170                 175

Tyr Thr Leu Ala Leu Thr Gly Lys Val Asn Pro Tyr Ser Ala Gly Met
                180                 185                 190

Gly Leu Met Pro Gly His Val Tyr Arg Ala Leu Tyr Pro Cys Pro Leu
            195                 200                 205

His Gly Ile Ser Glu Asp Asp Ala Ile Ala Ser Ile His Arg Ile Phe
            210                 215                 220

Lys Asn Asp Ala Ala Pro Glu Asp Ile Ala Ile Val Ile Glu Pro
225                 230                 235                 240

Val Gln Gly Glu Gly Gly Phe Tyr Ala Ser Ser Pro Ala Phe Met Gln
                245                 250                 255

Arg Leu Arg Ala Leu Cys Asp Glu His Gly Ile Met Leu Ile Ala Asp
                260                 265                 270

Glu Val Gln Ser Gly Ala Gly Arg Thr Gly Thr Leu Phe Ala Met Glu
            275                 280                 285

Gln Met Gly Val Ala Pro Asp Leu Thr Thr Phe Ala Lys Ser Ile Ala
290                 295                 300

Gly Gly Phe Pro Leu Ala Gly Val Thr Gly Arg Ala Glu Val Met Asp
305                 310                 315                 320

Ala Val Ala Pro Gly Gly Leu Gly Gly Thr Tyr Ala Gly Asn Pro Ile
                325                 330                 335

Ala Cys Val Ala Ala Leu Glu Val Leu Lys Val Phe Glu Gln Glu Asn
                340                 345                 350

Leu Leu Gln Lys Ala Asn Asp Leu Gly Gln Lys Leu Lys Asp Gly Leu
                355                 360                 365

Leu Ala Ile Ala Glu Lys His Pro Glu Ile Gly Asp Val Arg Gly Leu
            370                 375                 380

Gly Ala Met Ile Ala Ile Glu Leu Phe Glu Asp Gly Asp His Asn Lys
385                 390                 395                 400

Pro Asp Ala Lys Leu Thr Ala Glu Ile Val Ala Arg Ala Arg Asp Lys
                405                 410                 415

Gly Leu Ile Leu Leu Ser Cys Gly Pro Tyr Tyr Asn Val Leu Arg Ile
                420                 425                 430

Leu Val Pro Leu Thr Ile Glu Asp Ala Gln Ile Arg Gln Gly Leu Glu
            435                 440                 445

Ile Ile Ser Gln Cys Phe Asp Glu Ala Lys Gln
        450                 455
```

<210> SEQ ID NO 7
<211> LENGTH: 40
<212> TYPE: DNA
<213> ORGANISM: Artificial
<220> FEATURE:
<223> OTHER INFORMATION: primer acdS-for

<400> SEQUENCE: 7

| tctgcgcgta atctgctgct tgagcgcaac gcaattaatg | 40 |

<210> SEQ ID NO 8
<211> LENGTH: 33
<212> TYPE: DNA
<213> ORGANISM: Artificial
<220> FEATURE:
<223> OTHER INFORMATION: primer gabT-Rev

<400> SEQUENCE: 8

| cgattctaga ctactgcttc gcctcatcaa aac | 33 |

<210> SEQ ID NO 9
<211> LENGTH: 1535
<212> TYPE: DNA
<213> ORGANISM: Artificial
<220> FEATURE:
<223> OTHER INFORMATION: gabT fragment 2

<400> SEQUENCE: 9

| tctgcgcgta atctgctgct tgagcgcaac gcaattaatg tgagttagct cactcattag | 60 |
| gcaccccagg ctttacactt tatgcttccg gctcgtatgt tgtgtggaat tgtgagcgga | 120 |
| taacaatttc acacaggaaa cagctatgac catgattacg ccaagcgcgc aattaaccct | 180 |
| cactaaaggg aacaaaagct gggtaccggg ccccccctcg aggtcgacgg tatcgataag | 240 |
| cttaatgaac agcaataaag agttaatgca gcgccgcagt caggcgattc cccgtggcgt | 300 |
| tgggcaaatt cacccgattt tcgctgaccg cgcggaaaac tgccgggtgt gggacgttga | 360 |
| aggccgtgag tatcttgatt tcgcgggcgg gattgcggtg ctcaataccg gcacctgca | 420 |
| tccgaaggtg gtggccgcgg tggaagcgca gttgaaaaaa ctgtcgcaca cctgcttcca | 480 |
| ggtgctggct tacagccgt atctggagct gtgcgagatt atgaatcaga aggtgccggg | 540 |
| cgatttcgcc aagaaaacgc tgctggttac gaccggttcc gaagcggtgg aaaacgcggt | 600 |
| aaaaatcgcc cgcgccgcca ccaaacgtag cggcaccatc gcttttagcg gcgcgtatca | 660 |
| cgggcgcacg cattacacgc tggcgctgac cggcaaggtg aatccgtact ctgcgggcat | 720 |
| ggggctgatg ccgggtcatg tttatcgcgc gctttatcct tgcccgctgc acggcataag | 780 |
| cgaggatgac gctatcgcca gcatccaccg gatcttcaaa aatgatgccg cgccggaaga | 840 |
| tatcgccgcc atcgtgattg agccggttca gggcgaaggc ggtttctacg cctcgtcgcc | 900 |
| agcctttatg cagcgtttac gcgctctgtg tgacgagcac gggatcatgc tgattgccga | 960 |
| tgaagtgcag agcggcgcgg ggcgtaccgg cacgctgttt gcgatggagc agatgggcgt | 1020 |
| tgcgccggat cttaccacct ttgcgaaatc gatcgcgggc ggcttcccgc tggcgggcgt | 1080 |
| caccgggcgc gcggaagtaa tggatgccgt cgctccaggc ggtctgggcg cacctatgc | 1140 |
| gggtaacccg attgcctgcg tggctgcgct ggaagtgttg aaggtgtttg agcaggaaaa | 1200 |
| tctgctgcaa aaagccaacg atctggggca gaagttgaaa gacggattgc tggcgatagc | 1260 |
| cgaaaaacac ccggagatcg gcgacgtacg cgggctgggg gcgatgatcg ccattgagct | 1320 |
| gtttgaagac ggcgatcaca acaagccgga cgccaaactc accgccgaga tcgtggctcg | 1380 |
| cgcccgcgat aaaggcctga ttcttctctc ctgcggcccg tattacaacg tgctgcgcat | 1440 |
| ccttgtaccg ctcaccattg aagacgctca gatccgtcag ggtctggaga tcatcagcca | 1500 |
| gtgtttgat gaggcgaagc agtagtctag aatcg | 1535 |

<210> SEQ ID NO 10
<211> LENGTH: 30
<212> TYPE: DNA
<213> ORGANISM: Artificial
<220> FEATURE:
<223> OTHER INFORMATION: primer amp_ter-for2

<400> SEQUENCE: 10
gctagaattc ctgtcagacc aagtttactc                                    30

<210> SEQ ID NO 11
<211> LENGTH: 40
<212> TYPE: DNA
<213> ORGANISM: Artificial
<220> FEATURE:
<223> OTHER INFORMATION: primer amp_ter-rev2

<400> SEQUENCE: 11
cattaattgc gttgcgctca agcagcagat tacgcgcaga                         40

<210> SEQ ID NO 12
<211> LENGTH: 231
<212> TYPE: DNA
<213> ORGANISM: Artificial
<220> FEATURE:
<223> OTHER INFORMATION: amp-term fragment

<400> SEQUENCE: 12
gaattcctgt cagaccaagt ttactcatat atactttaga ttgatttaaa acttcatttt    60
taatttaaaa ggatctaggt gaagatcctt tttgataatc tcatgaccaa aatcccttaa  120
cgtgagtttt cgttccactg agcgtcagac cccgtagaaa agatcaaagg atcttcttga  180 gatcctttt ttctgcgcgt aatctgctgc ttgagcgcaa cgcaattaat g            231

<210> SEQ ID NO 13
<211> LENGTH: 1017
<212> TYPE: DNA
<213> ORGANISM: Pseudomonas sp.
<220> FEATURE:
<223> OTHER INFORMATION: ACC deaminase gene
<220> FEATURE:
<221> NAME/KEY: CDS
<222> LOCATION: (1)..(1017)

<400> SEQUENCE: 13 atg aac ctg caa cga ttc cct cgt tac ccg ctg act ttc ggg ccg acg     48
Met Asn Leu Gln Arg Phe Pro Arg Tyr Pro Leu Thr Phe Gly Pro Thr
1               5                   10                  15 cca atc caa ccg cta gcg cgt ctg agc aag cac ctc ggc ggc aaa gtg     96
Pro Ile Gln Pro Leu Ala Arg Leu Ser Lys His Leu Gly Gly Lys Val
            20                  25                  30 cat ctg tat gcg aaa cgc gaa gac tgc aac agc ggc ctg gcg ttc ggt    144
His Leu Tyr Ala Lys Arg Glu Asp Cys Asn Ser Gly Leu Ala Phe Gly
        35                  40                  45 ggc aac aag aca cgc aag ctc gaa tat ctg atc cct gaa gcg ctt gct    192
Gly Asn Lys Thr Arg Lys Leu Glu Tyr Leu Ile Pro Glu Ala Leu Ala
    50                  55                  60 cag ggt tgc gac acg ctc gtg tcg atc ggc ggc att cag tcg aac cag    240
Gln Gly Cys Asp Thr Leu Val Ser Ile Gly Gly Ile Gln Ser Asn Gln
65                  70                  75                  80 acg cgc cag gtg gcg gcc gtg gcg gct cat ctg ggc atg aag tgc gtg    288
Thr Arg Gln Val Ala Ala Val Ala Ala His Leu Gly Met Lys Cys Val
                85                  90                  95

```
ctg gtg cag gag aac tgg gtc aac tat tcg gac gca gtc tac gac cgc    336
Leu Val Gln Glu Asn Trp Val Asn Tyr Ser Asp Ala Val Tyr Asp Arg
        100                 105                 110 gtc ggc aac atc cag atg tcg cgc att ctc ggc gcc gat gtt cgc ctc    384
Val Gly Asn Ile Gln Met Ser Arg Ile Leu Gly Ala Asp Val Arg Leu
            115                 120                 125 gtg ccc gac ggc ttc gac atc ggt ttt cgc agg agc tgg gag gat gcg    432
Val Pro Asp Gly Phe Asp Ile Gly Phe Arg Arg Ser Trp Glu Asp Ala
    130                 135                 140 ctg gaa agc gtg cgg gcg gcc ggc ggc aag ccg tat gcg att ccg gca    480
Leu Glu Ser Val Arg Ala Ala Gly Gly Lys Pro Tyr Ala Ile Pro Ala
145                 150                 155                 160 ggc tgc tcg gat cac ccg ctc ggc ggc ctg ggt ttc gtc ggc ttc gcg    528
Gly Cys Ser Asp His Pro Leu Gly Gly Leu Gly Phe Val Gly Phe Ala
                165                 170                 175 gag gag gtg cgg gcg cag gaa gcc gaa ttg ggc ttc aaa ttc gac tat    576
Glu Glu Val Arg Ala Gln Glu Ala Glu Leu Gly Phe Lys Phe Asp Tyr
            180                 185                 190 gtc gtc gtg tgt tcc gtg acc ggc agc acg cag gcc ggc atg gtg gtg    624
Val Val Val Cys Ser Val Thr Gly Ser Thr Gln Ala Gly Met Val Val
    195                 200                 205 ggc ttc gcc gct gac ggc cgc gcc gat cgc gtg atc ggc gtc gac gct    672
Gly Phe Ala Ala Asp Gly Arg Ala Asp Arg Val Ile Gly Val Asp Ala
210                 215                 220 tcg gcc aaa ccc gcg cag acg cgc gag cag atc acc cgc atc gcg aga    720
Ser Ala Lys Pro Ala Gln Thr Arg Glu Gln Ile Thr Arg Ile Ala Arg
225                 230                 235                 240 cag acc gcg gag aaa gtc ggc ctg gag cgc gat atc atg cgg gcc gac    768
Gln Thr Ala Glu Lys Val Gly Leu Glu Arg Asp Ile Met Arg Ala Asp
                245                 250                 255 gtg gtg ctc gac gag cgc ttc gcg ggt ccg gaa tac gga ttg ccg aac    816
Val Val Leu Asp Glu Arg Phe Ala Gly Pro Glu Tyr Gly Leu Pro Asn
            260                 265                 270 gaa ggc acg ctg gaa gcg atc cgc ttg tgc gcg cgc acg gag ggc atg    864
Glu Gly Thr Leu Glu Ala Ile Arg Leu Cys Ala Arg Thr Glu Gly Met
    275                 280                 285 ctg acc gat ccc gtc tac gaa ggc aaa tcg atg cac ggc atg atc gaa    912
Leu Thr Asp Pro Val Tyr Glu Gly Lys Ser Met His Gly Met Ile Glu
290                 295                 300 atg gtg cgc aac ggc gaa ttt ccg gaa ggc tcg cgc gtg ctg tat gcg    960
Met Val Arg Asn Gly Glu Phe Pro Glu Gly Ser Arg Val Leu Tyr Ala
305                 310                 315                 320 cac ctc ggc ggg gtg ccg gcg ttg aac ggc tac agc ttt atc ttc cga   1008
His Leu Gly Gly Val Pro Ala Leu Asn Gly Tyr Ser Phe Ile Phe Arg
                325                 330                 335 gac ggc tga                                                       1017
Asp Gly

<210> SEQ ID NO 14
<211> LENGTH: 338
<212> TYPE: PRT
<213> ORGANISM: Pseudomonas sp.
<220> FEATURE:
<223> OTHER INFORMATION: ACC deaminase protein

<400> SEQUENCE: 14

Met Asn Leu Gln Arg Phe Pro Arg Tyr Pro Leu Thr Phe Gly Pro Thr
1               5                   10                  15

Pro Ile Gln Pro Leu Ala Arg Leu Ser Lys His Leu Gly Gly Lys Val
            20                  25                  30
```

-continued

His Leu Tyr Ala Lys Arg Glu Asp Cys Asn Ser Gly Leu Ala Phe Gly
                35                  40                  45

Gly Asn Lys Thr Arg Lys Leu Glu Tyr Leu Ile Pro Glu Ala Leu Ala
 50                  55                  60

Gln Gly Cys Asp Thr Leu Val Ser Ile Gly Ile Gln Ser Asn Gln
65                  70                  75                  80

Thr Arg Gln Val Ala Ala Val Ala Ala His Leu Gly Met Lys Cys Val
                85                  90                  95

Leu Val Gln Glu Asn Trp Val Asn Tyr Ser Asp Ala Val Tyr Asp Arg
            100                 105                 110

Val Gly Asn Ile Gln Met Ser Arg Ile Leu Gly Ala Asp Val Arg Leu
            115                 120                 125

Val Pro Asp Gly Phe Asp Ile Gly Phe Arg Arg Ser Trp Glu Asp Ala
            130                 135                 140

Leu Glu Ser Val Arg Ala Ala Gly Gly Lys Pro Tyr Ala Ile Pro Ala
145                 150                 155                 160

Gly Cys Ser Asp His Pro Leu Gly Gly Leu Gly Phe Val Gly Phe Ala
                165                 170                 175

Glu Glu Val Arg Ala Gln Glu Ala Glu Leu Gly Phe Lys Phe Asp Tyr
            180                 185                 190

Val Val Val Cys Ser Val Thr Gly Ser Thr Gln Ala Gly Met Val Val
            195                 200                 205

Gly Phe Ala Ala Asp Gly Arg Ala Asp Arg Val Ile Gly Val Asp Ala
210                 215                 220

Ser Ala Lys Pro Ala Gln Thr Arg Glu Gln Ile Thr Arg Ile Ala Arg
225                 230                 235                 240

Gln Thr Ala Glu Lys Val Gly Leu Glu Arg Asp Ile Met Arg Ala Asp
                245                 250                 255

Val Val Leu Asp Glu Arg Phe Ala Gly Pro Glu Tyr Gly Leu Pro Asn
            260                 265                 270

Glu Gly Thr Leu Glu Ala Ile Arg Leu Cys Ala Arg Thr Glu Gly Met
            275                 280                 285

Leu Thr Asp Pro Val Tyr Glu Gly Lys Ser Met His Gly Met Ile Glu
            290                 295                 300

Met Val Arg Asn Gly Glu Phe Pro Glu Gly Ser Arg Val Leu Tyr Ala
305                 310                 315                 320

His Leu Gly Gly Val Pro Ala Leu Asn Gly Tyr Ser Phe Ile Phe Arg
                325                 330                 335

Asp Gly

<210> SEQ ID NO 15
<211> LENGTH: 17
<212> TYPE: DNA
<213> ORGANISM: Artificial
<220> FEATURE:
<223> OTHER INFORMATION: primer GUSF

<400> SEQUENCE: 15
atccacgccg tattcgg                                                  17

<210> SEQ ID NO 16
<211> LENGTH: 20
<212> TYPE: DNA

```
<213> ORGANISM: Artificial
<220> FEATURE:
<223> OTHER INFORMATION: primer GUSR

<400> SEQUENCE: 16
catgaagatg cggacttacg                                              20
```